US008877240B1

(12) United States Patent
Moore

(10) Patent No.: US 8,877,240 B1
(45) Date of Patent: Nov. 4, 2014

(54) TABLET BINDING COMPOSITIONS

(71) Applicant: Ryan Giffin Moore, Lilburn, GA (US)

(72) Inventor: Ryan Giffin Moore, Lilburn, GA (US)

(73) Assignee: ChemLink Laboratories, LLC, Kennesaw, GA (US)

(*) Notice: Subject to any disclaimer, the term of this patent is extended or adjusted under 35 U.S.C. 154(b) by 0 days.

(21) Appl. No.: 14/151,564

(22) Filed: Jan. 9, 2014

(51) Int. Cl.
*A61K 9/20* (2006.01)
*A61K 9/50* (2006.01)
*A61K 45/00* (2006.01)
*A01N 25/00* (2006.01)
*C11D 17/00* (2006.01)

(52) U.S. Cl.
CPC .................................. *C11D 17/0073* (2013.01)
USPC ............ 424/464; 424/499; 424/465; 514/784

(58) Field of Classification Search
USPC ........................... 424/464, 499, 465; 514/784
See application file for complete search history.

(56) References Cited

U.S. PATENT DOCUMENTS

| | | | | |
|---|---|---|---|---|
| 2,696,441 | A | 12/1959 | Kmieciak et al. | |
| 3,898,344 | A | 8/1975 | Masuoka et al. | |
| 4,099,912 | A | 7/1978 | Ehrlich | |
| 4,515,705 | A | 5/1985 | Moeddel | |
| 4,634,551 | A | 1/1987 | Burns et al. | |
| 4,642,197 | A | 2/1987 | Kruse et al. | |
| 4,654,341 | A | 3/1987 | Nelson et al. | |
| 4,897,212 | A | 1/1990 | Kruse et al. | |
| 4,915,854 | A | 4/1990 | Mao et al. | |
| 5,225,100 | A | 7/1993 | Fry et al. | |
| 5,756,440 | A | 5/1998 | Watanabe et al. | |
| 5,858,959 | A | 1/1999 | Surutzidis et al. | |
| 6,397,862 | B1 | 6/2002 | DeSenna et al. | |
| 6,451,746 | B1 | 9/2002 | Moore et al. | |
| 6,491,947 | B2 | 12/2002 | Moore et al. | |
| 6,664,226 | B2 | 12/2003 | Jacques et al. | |
| 6,689,305 | B1 | 2/2004 | Fernholz et al. | |
| 6,849,591 | B1 | 2/2005 | Boeckh et al. | |
| 6,974,789 | B1 * | 12/2005 | Whitaker et al. | 510/294 |
| 7,153,817 | B2 | 12/2006 | Binder | |
| 7,598,217 | B2 | 10/2009 | Burg et al. | |
| 8,357,647 | B2 | 1/2013 | Sharma et al. | |
| 8,426,350 | B2 | 4/2013 | Geret et al. | |
| 8,454,709 | B2 | 6/2013 | Man et al. | |
| 8,551,932 | B2 | 10/2013 | Barger et al. | |
| 8,652,434 | B2 | 2/2014 | Moore et al. | |
| 2002/0081264 | A1 | 6/2002 | Moore et al. | |
| 2002/0127183 | A1 | 9/2002 | DeSenna et al. | |
| 2002/0132746 | A1 | 9/2002 | DeSenna et al. | |
| 2003/0032573 | A1 | 2/2003 | Tanner et al. | |
| 2003/0100101 | A1 | 5/2003 | Huth et al. | |
| 2003/0171245 | A1 | 9/2003 | Goovaerts et al. | |
| 2005/0113279 | A1 | 5/2005 | Desmarescaux et al. | |
| 2008/0069877 | A1 * | 3/2008 | Olsen et al. | 424/465 |
| 2011/0118166 | A1 | 5/2011 | Tjelta et al. | |
| 2012/0142576 | A1 | 6/2012 | Bartelme et al. | |
| 2012/0208740 | A1 | 8/2012 | Moore et al. | |
| 2012/0219513 | A1 | 8/2012 | Moore et al. | |
| 2013/0109609 | A1 | 5/2013 | Smith et al. | |

FOREIGN PATENT DOCUMENTS

| | | | |
|---|---|---|---|
| EP | 2161022 | A1 * | 3/2010 |

* cited by examiner

*Primary Examiner* — Abigail Fisher
(74) *Attorney, Agent, or Firm* — McKenna Long & Aldridge LLP; Frank J. Miskiel; Matthew T. Bailey

(57) ABSTRACT

Provided are tablet binding compositions for binding cleaning and/or disinfecting formulation components into tablets. The tablet binding compositions are suitable replacements for traditional tablet binder compounds, such as boric acid or zeolites. The tablet binding compositions provided herein can produce tablets of increased hardness at lower compression forces and, when dissolved, yield solutions of increased clarity compared to some traditional binder compounds. Also provided are processes for preparing the tablet binding compositions and methods for formation of tablets containing the tablet binding compositions.

28 Claims, No Drawings

TABLET BINDING COMPOSITIONS

FIELD

The present invention relates to tablet binding compositions for preparing cleaning and/or disinfectant compositions in the form of tablets, and to tablets containing the tablet binding compositions.

BACKGROUND

Cleaning compositions in solid form, such as tablet form, are known in the art (e.g., see U.S. Pat. No. 4,099,912 (Ehrlich), U.S. Pat. No. 4,642,197 (Kruse et al.), U.S. Pat. No. 4,654,341 (Nelson et al.), U.S. Pat. No. 4,897,212 (Kruse et al.), U.S. Pat. No. 5,225,100 (Fry et al.), U.S. Pat. No. 5,756,440 (Watanabe et al.), U.S. Pat. No. 5,858,959 (Surutzidis et al.), U.S. Pat. No. 6,664,226 (Jacques et al.), U.S. Pat. No. 6,689,305 (Fernholz et al.), U.S. Pat. No. 7,153,817 (Binder), U.S. Pat. No. 7,598,217 (Burg et al.), U.S. Pat. No. 8,357,647 (Sharma et al.), and U.S. Pat. No. 8,426,350 (Geret et al.) and U.S. Pat. App. Pub. Nos. US2003/0100101 (Huth et al.), US2003/0171245 (Goovaerts et al.), US2005/0113279 (Desmarescaux et al.), US2011/0118166 (Tjelta et al.), US2012/0142576 (Bartelme et al.), and US2013/0109609 (Smith et al.)). Tablets provide individual doses of cleaning compositions. Many consumers find tablet forms of cleaning compositions to be more convenient and in some applications more attractive than traditional liquid or powder forms. Tablets are more compact, and thus facilitate transport and storage. Tablets also eliminate the need for measuring, resulting in precise dosing and avoiding wasteful overdosing or underdosing. Tablets also make the compositions easier to handle and dispense. For these reasons, cleaning products in tablet form have become very popular.

Tablet binders are compounds used to bind together the ingredients and hold together the structure of the tablets. Conventional binders used in the formation of tablets of cleaning compositions have been found wanting in several respects. Some binders exhibit undesirable friable properties when subjected to high compression, thus causing difficulties in packaging and shipping as well as increasing costs due to losses of uniform tablet size and decreased aesthetic appeal. Other binders result in tablet compositions characterized as having a low rate of dissolution or result in solutions that are hazy or opaque or that leave a residue upon drying.

Among the conventional tablet binders are borates, such as boric acid, sodium tetraborate decahydrate and sodium perborate. The borate compounds have been used extensively in making a multitude of cleaning, disinfecting, and personal care compositions.

Traditionally, boric acid has been used in tablet compositions because of its ability to act as both a tablet binder and a mold release lubricant. Boric acid also is a very inexpensive material. Boric acid is easy to use in production because it simply needs to be dry mixed into the final tablet composition. Boric acid also is completely soluble in water, which is an important feature when producing products like glass cleaners and detergents. Borates, however, are increasingly becoming a concern for environmental and human health and safety. Borates have a potential to pollute waterways and ground soil if not used and disposed of properly. Due to these concerns, many companies are opting to remove borates completely from their formulations. The complete removal of borates from these compositions presents a challenge to the tablet industry.

Zeolites, which include crystalline aluminum silicates, also have been used as binders for tablets, particularly for detergent compositions, where they can serve a dual function as binder and builder. A problem with using zeolites as tablet binder is that solutions resulting from the dissolved tablets often exhibit a haze or cloudy solution, which for many cleaning compositions is deemed to be unsatisfactory. The solutions when dried also can result in a hazy surface.

Accordingly, a need exists for tablet binding compositions that allow tablet formation without the use of traditional binders, such as borates and zeolites. In addition, a need exists for a tablet binding composition that results in a tablet that is resistant to crumbling or powdering during manufacturing, packaging and shipping processes.

SUMMARY

Among the objects herein, provided are tablet binding compositions that can replace borates and other traditional binders in tablet compositions. The tablet binding compositions provided herein have the same or similar binding and lubrication action on tablet compositions as boric acid. The tablet binding compositions provided herein also retain the low cost structure and ease of use as borates, such as boric acid, that other binding compounds and technologies do not offer. The tablet binding compositions provided herein are safer than borate-containing binders for the production environment and for the consumers using the products containing the binder compositions. The tablet binding compositions provided herein also will allow for reduced product warnings on the label. The tablet binding compositions provided herein also should result in grant of approval from the US EPA Design for the Environment (DfE) group to brand tablet products containing the tablet binding compositions provided herein with their logo.

Another object of the present invention to provide a tablet binding composition that completely replaces borates. Another object of the invention is to provide a tablet binding composition that reduces the number of components needed in the production of readily dissolvable tablets. Another object of the present invention is to provide a tablet binding composition that binds components of a cleaning composition during compression and releases the tablet from the press mold without breaking, sticking or picking. The tablet binding compositions provided herein exhibit mold release properties similar to those exhibited by boric acid.

Another object is to facilitate the manufacture of tablets having the above improved properties by a simple and economical process. The tablet binding compositions provided herein allow for tablet production that entails essentially only two principal steps: the mixing of all the ingredients and then compressing this mixture into a tablet. The tablet binding compositions provided herein exhibit good dry powder flowability alone or when combined with other components of a formulation. Another object of the present invention is to provide a tablet binding composition that produces tablets with acceptable hardness and visual aesthetics, such as smooth face surfaces and good edge definition. The tablet binding compositions provided herein produce tablets that exhibit tablet hardness values within what the tablet industry generally considers an optimal operating range for tablet hardness and having the desired product aesthetics and dissolution characteristics. The tablet binding compositions provided herein produce tablets that when dissolve yield solutions with good clarity. The tablet binding compositions provided herein produce tablets that exhibit a weight loss percentage of less than 0.5% thereby minimizing loss due to waste. The tablet binding compositions provided herein produce tablets of acceptable hardness at compression forces significantly less than that required using traditional binders, such as borates or zeolites. In some applications, tablets having acceptable hardness can be produced at compression forces of less than 2000 PSI, such as 1750 PSI. Also provided are methods of producing tablets having good tablet hardness values using lower compression forces, the methods including combining a tablet binding composition provided herein with the other components of the formulation, mixing the components to produce a uniform mix and compressing the mix in a humidity controlled environment to produce a tablet. These and other objects of the invention will become apparent from the following description and disclosure.

A. DEFINITIONS

Unless defined otherwise, all technical and scientific terms used herein have the same meaning as is commonly understood by one of skill in the art to which the inventions belong.

All patents, patent applications, published applications and publications, websites and other published materials referred to throughout the entire disclosure herein, unless noted otherwise, are incorporated by reference in their entirety. In the event that there are a plurality of definitions for terms herein, those in this section prevail.

As used here, the singular forms "a," "an" and "the" include plural referents unless the context clearly dictates otherwise.

As used herein, ranges and amounts can be expressed as "about" a particular value or range. "About" also includes the exact amount. Hence "about 5 percent" means "about 5 percent" and also "5 percent." "About" means within typical experimental error for the application or purpose intended.

In the examples, and throughout this disclosure, all parts and percentages are by weight (wt %) and all temperatures are in ° C., unless otherwise indicated.

As used herein, the phrase "based on the weight of the composition" with reference to % refers to wt % (mass % or (w/w) %).

As used herein, a "C6 saccharide derivative sequestrant" refers to an amino derivative or a hydrogenated or an oxidized derivative of a sugar that contains six C atoms (aldohexoses and ketohexoses). Exemplary of the C6 saccharide derivative sequestrants are the amino hexoses, hexitols, aldonic acids and salts thereof, aldonic acid lactones and salts thereof, hexose-δ-lactones and salts thereof, and saccharic acids and salts thereof.

As used herein, "amino hexose" refers to a sugar or saccharide having six C atoms that contains an amino group in place of a hydroxyl group. Glucosamine, galactosamine, mannosamine and derivatives of amino containing sugars, such as N-acetylglucosamine, N-acetyl mannosamine and N-acetyl galactosamine are examples of amino hexoses.

As used herein, "hexitol" refers to a sugar containing six C atoms in which the aldehyde or ketone group has been reduced (hydrogenated) to an alcohol. Examples of hexitols include allitol, altritol (talitol), fucitol, galactitol (dulcitol), glucitol (sorbitol), iditol, and mannitol.

As used herein, an "aldonic acid" refers to any one of a family of sugar acids obtained by oxidation of the aldehyde functional group of an aldose to form a carboxylic acid functional group.

As used herein, an "aldonic acid lactone" refers to a lactone of an aldonic acid. The term "lactone" refers a cyclic ester that is the condensation product of a hydroxy group and a carboxylic acid group in the same molecule.

As used herein, a "saccharic acid" refers to an oxidized sugar usually produced by oxidizing a sugar with nitric acid, resulting in a compound having the formula $C_6H_{10}O_8$. In this oxidized form of sugar, the carbon atom bearing the primary hydroxyl group and the aldehydic carbon atom are oxidized to carboxylic acid groups.

As used herein, "tablet" refers to any unitary solid form preparation where the dosage of each unit is fixed by size and weight. Tablets can be of any shape and can be prepared using any method known in the art, including compression, casting, briquetting, injection molding and extrusion.

As used herein, a "binder" or "tablet binding composition" refers to a compound or composition that holds together the structure of a tablet. Tablet binders or tablet binding compositions have the ability to bind together the other ingredients in a tablet after sufficient compression forces have been applied, and contribute to the integrity of the tablet.

As used herein, a "surfactant" refers to a substance or compound that reduces surface tension when dissolved in water or water solutions, or that reduces interfacial tension between two liquids, or between a liquid and a solid. The term "surfactant" thus includes cationic, anionic, nonionic, zwitterionic, and amphoteric agents and combinations thereof.

As used herein, "PSI" refers to pounds per square inch.

As used herein, "mean particle size" refers to the number average diameter of a particle calculated from the particle size distribution for a collection of particles.

B. TABLET BINDING COMPOSITIONS

Borates and zeolites are traditional tableting binding compounds. There also are many examples of tablet binding compounds that are polymers and co-polymers. These polymer and co-polymer compounds typically are only economically viable in the pharmaceutical setting due to the cost of these polymers. These polymer-based tablet binding compounds are typically not soluble in water and carry significant environmental concerns. The polymer-based tablet binding compounds typically used in pharmaceutical tableting processes tend to require wet granulation processes or a spray drying technique, which adds further costs to the manufacturing process. The tablet binding compositions provided herein can include a liquid component but do not require a wet granulation technique, which generally require both a drying step and a grinding step before tablet compression can begin. The tablet binding compositions provided herein avoids these costly steps and achieves acceptable tablet binding required for effective production by simply blending the tablet binding composition into the final tablet composition and going straight to tablet formation, such as via compression.

C6 Saccharide Derivative Sequestrants

The tablet binding compositions provided herein contain a C6 saccharide derivative sequestrant and an acetate salt. Exemplary of the C6 saccharide derivative sequestrants are the amino hexoses and hydrogenated forms and oxidized forms of the aldohexoses, e.g., derivatives of the D and L isomers of allose, altrose, galactose, glucose, gulose, idose, mannose, and talose, and the hydrogenated forms and oxidized forms of the ketohexoses e.g., the D and L isomers of fructose, psicose, sorbose and tagatose. These compounds can be included in the composition singly or in combination of two or more species. The C6 saccharide derivative sequestrants generally are selected to be in an anhydrous form, such as an anhydrous crystalline or anhydrous powder form. Although hydrated crystalline forms could be used, the water of hydration of the sequestrant could migrate through the finished tablet, which could negatively impact shelf life of the tablet. In addition, the hydrated forms of some of the C6 saccharide derivative sequestrants are hygroscopic, which can negatively impact on tablet formation and/or stability. The tablet binding compositions provided herein also can contain only a C6 saccharide derivative sequestrant and an acetate salt.

In some applications, the C6 saccharide derivative sequestrant is or can contain an amino hexose. Exemplary amino hexoses include glucosamine, galactosamine, mannosamine and fucosamine. In some applications, the tablet binding composition contains glucosamine, galactosamine, mannosamine or fucosamine or a combination thereof. In some applications, the C6 saccharide derivative sequestrant is or can contain glucosamine. Amino hexoses are commercially available (e.g., from Cargill Incorporated, Minneapolis, Minn., USA; Glycoteam GmbH i. L., Hamburg, Germany; and 3B Scientific Corporation, Libertyville, Ill., USA). The C6 saccharide derivative sequestrant can contain one or more amino hexoses in combination with another C6 saccharide derivative sequestrant.

In some applications, the C6 saccharide derivative sequestrant is or can contain a hydrogenated aldohexose or ketohexose, examples of which include any of the hexitols, such as allitol, altritol (talitol), fucitol, galactitol (dulcitol), glucitol (sorbitol), iditol, and mannitol. Any combination of the hexitols can be used as the C6 saccharide derivative sequestrant. In some applications, the C6 saccharide derivative sequestrant is or contains a hexitol selected from among galactitol, glucitol and mannitol and combinations thereof. In some applications, the C6 saccharide derivative sequestrant is or contains d-glucitol. Hexitols are commercially available (e.g., from EMD Millipore, a division of Merck KGaA, Darmstadt, Germany, Archer Daniels Midland Company, Decatur, Ill., USA, Santa Cruz Biotechnology, Inc., Santa Cruz, Calif., USA, and BOC Sciences, Shirley, N.Y., USA). The C6 saccharide derivative sequestrant can contain one or more hexitols in combination with another C6 saccharide derivative sequestrant.

In some applications, the C6 saccharide derivative sequestrant is or can contain an oxidized C6 saccharide. The oxidized C6 saccharide can be an aldonic acid or a salt thereof. Exemplary aldonic acids include allonic acid, altronic acid, fuconic acid, galactonic acid, gluconic acid, gulonic acid, idonic acid, mannonic acid, sorbonic acid and talonic acid. Exemplary salts include alkali metal salts such as sodium salts and potassium salts; alkaline earth metal salts such as calcium salts and magnesium salts; and organic amine salts such as ammonium salts, triethylamine salts and triethanolamine salts. In some applications, the C6 saccharide derivative sequestrant can contain an alkali metal salt of an aldonic acid. In some applications, the alkali metal salt is a sodium or potassium salt of an aldonic acid. In some applications, the C6 saccharide derivative sequestrant contains one or a combination of potassium allonate, potassium altronate, potassium fuconate, potassium galactonate, potassium gluconate, potassium gulonate, potassium idonate, potassium mannonate, potassium sorbonate, potassium talonate, sodium allonate, sodium altronate, sodium fuconate, sodium galactonate, sodium gluconate, sodium gulonate, sodium idonate, sodium mannonate, sodium sorbonate and sodium talonate. In some applications, the C6 saccharide derivative sequestrant is or contains sodium gluconate or potassium gluconate. Aldonic acids and their lactones are commercially available (e.g., from NOAH Technologies Corporation, San Antonio, Tex., USA, Alfa Chemical Corp., Kings Point, N.Y., USA, Jungbunzlauer, Inc., Newton Center, Mass., ADM Food Additives, Decatur, Ill., USA, Cargill Texturizing Solutions, Wayzata, Minn., USA, and Spectrum Chemicals & Laboratory Products, Gardena, Calif., USA). The C6 saccharide derivative sequestrant can contain one or more aldonic acids or salts thereof in combination with another C6 saccharide derivative sequestrant.

In some applications, the C6 saccharide derivative sequestrant is or can contain an oxidized C6 saccharide that is an aldonic acid lactone. Exemplary aldonic acid lactones include allonolactone, altronolactone, gluconolactone, mannolactone, gulonolactone, idonolactone, galactonolactone, talonolactone. In some applications, the C6 saccharide derivative sequestrant is or contains an aldonic acid lactone selected from among gluconolactone, mannolactone, gulonolactone and galactonolactone and combinations thereof. In some applications, the C6 saccharide derivative sequestrant is or contains a gluconolactone. The C6 saccharide derivative sequestrant can contain one or more aldonic acid lactones in combination with another C6 saccharide derivative sequestrant.

In some applications, the C6 saccharide derivative sequestrant is or can contain an aldonic acid lactone that is a hexose-δ-lactone. Exemplary of the hexose-δ-lactones is glucono-delta-lactone. Hexose-δ-lactones and their lactones are commercially available (e.g., from Jungbunzlauer, Inc., Newton Center, Mass., and EMD Millipore, a division of Merck KGaA, Darmstadt, Germany). In some applications, the C6 saccharide derivative sequestrant is or can contain glucono-delta-lactone, alone or in combination with another C6 saccharide derivative sequestrant.

In some applications, the C6 saccharide derivative sequestrant is or can contain an oxidized C6 saccharide that is a saccharic acid or a salt thereof. Exemplary saccharic acids include glucaric acid, galactaric acid and mannaric acid. In some applications, the C6 saccharide derivative sequestrant is or contains glucaric acid, sodium glucarate, potassium glucarate or a combination thereof. Saccharic acids and their salts are commercially available (e.g., from Rivertop Renewables, Missoula, Mont., USA, Carbone Scientific Co., Ltd., London, UK, and Spectrum Chemical Mfg. Corp., Gardena, Calif., USA). The C6 saccharide derivative sequestrant can contain one or more saccharic acid or a salt thereof in combination with another C6 saccharide derivative sequestrant.

The C6 saccharide derivative sequestrant can be selected to be anhydrous. The C6 saccharide derivative sequestrant can be selected to be in a fine grind or fine crystalline form. The C6 saccharide derivative sequestrant can be selected to be in an anhydrous fine grind or anhydrous crystalline form.

The particles or crystals of the C6 saccharide derivative sequestrants generally are available in different particle sizes. In some applications, the C6 saccharide derivative sequestrant selected for the tablet binding compositions provided herein have a mean particle size in the range of from about 100 μm to about 1200 μm. In some applications, the C6 saccharide derivative sequestrant selected for the tablet binding compositions provided herein have a mean particle size in the range of from about 50 μm to about 500 μm or in the range of from about 100 μm to about 1000 μm or in the range of from about 150 μm to about 950 μm. In some applications, the C6 saccharide derivative sequestrant selected for the tablet binding compositions provided herein have a particle size distribution in the range of from about 100 μm to about 1200 μm. In some applications, the C6 saccharide derivative sequestrant has a particle size greater than 50 μm, or greater than 100 μm, or greater than 150 μm, or greater than 200 μm, or greater than 250 μm, or greater than 300 μm, or greater than 350 μm, or greater than 400 μm, or greater than 450 μm, or greater than 500 μm, or greater than 550 μm, or greater than 600 μm, or greater than 650 μm, or greater than 700 μm, or greater than 750 μm, or greater than 800 μm, or greater than 850 μm, or greater than 900 μm, or greater than 950 μm. In some applications, at least 70% of the particles of the C6 saccharide derivative sequestrant are greater than 150 μm. In some applications, at least 50% of the particles of the C6 saccharide derivative sequestrant are greater than 250 μm.

In some applications, the C6 saccharide derivative sequestrant has a particle size such that at least 90% passes through a U.S. Standard Mesh No. 20 sieve. In some applications, the C6 saccharide derivative sequestrant has a particle size such that at least 80% passes through a U.S. Standard Mesh No. 20 sieve. In some applications, the C6 saccharide derivative sequestrant has a particle size such that at least 70% passes through a U.S. Standard Mesh No. 20 sieve. In some applications, the C6 saccharide derivative sequestrant has a particle size such that at least 60% passes through a U.S. Standard Mesh No. 30 sieve. In some applications, the C6 saccharide derivative sequestrant has a particle size such that at least 10% passes through a U.S. Standard Mesh No. 30 sieve. In some applications, the C6 saccharide derivative sequestrant has a particle size such that at least 60% passes through a U.S. Standard Mesh No. 30 sieve. In some applications, the C6 saccharide derivative sequestrant has a particle size such that at least 50% is retained on a U.S. Standard Mesh No. 40 sieve. In some applications, the C6 saccharide derivative sequestrant has a particle size such that at least 70% is retained on a U.S. Standard Mesh No. 60 sieve. In some applications, the C6 saccharide derivative sequestrant has a particle size such that at least 80% is retained on a U.S. Standard Mesh No. 100 sieve.

The C6 saccharide derivative sequestrant can be present in the tablet binding compositions provided herein in an amount that is from at or about 15% to at or about 85% by weight of the composition. The C6 saccharide derivative sequestrant can be present in the tablet binding compositions provided herein in an amount that is from at or about 20% to at or about 80% by weight of the composition. In some applications, the C6 saccharide derivative sequestrant is present in an amount that is selected from among at least 15%, at least 20%, at least 25%, at least 30%, at least 35%, at least 40%, at least 45%, at least 50%, at least 55%, at least 60%, at least 65%, at least 70%, at least 75%, and at least 80% based on the weight of the composition. With respect to the acetate salt component of the tablet binding compositions provided herein, the C6 saccharide derivative sequestrant can be present in a ratio of from about 1:5 sequestrant:acetate to about 5:1 sequestrant:acetate. For example, the ratio of sequestrant:acetate can be selected from among 1:5, 1:4.75, 1:4.5, 1:4.25, 1:4, 1:3.75, 1:3.5, 1:3.25, 1:3, 1:2.75, 1:2.5, 1:3.25, 1:2, 1:1.75, 1:1.5, 1:1.25, 1:1, 1:1.25, 1:1.5, 1:1.75, 1:2, 1:2.25, 1:2.5, 1:2.75, 1:3, 1:3.25, 1:3.5, 1:3.75, 1:4, 1:4.24, 1:4.5, 1:4.75 and 1:5.

Acetate Salts

The tablet binding compositions provided herein include an acetate salt. It has been discovered that particular ratios of C6 saccharide derivative sequestrants to acetate salts provide binding and lubrication action on tablet compositions similar to or superior to that achieved using boric acid. Similar to boric acid, acetate salts are completely soluble in water. This invention also retains the low cost structure and ease of use of boric acid that other binding compounds and technologies do not offer. The use of the tablet binding compositions provided herein that include acetate salts in combination with a C6 saccharide derivative sequestrant in tablet compositions, instead of boric acid and its salts, is much safer for both the production environment and for the consumers using the products. The use of the tablet binding compositions provided herein in tablet compositions will allow for reduced product warnings on the label. For example, chronic exposure to boric acid can result in systemic toxicity. The new OSHA GHS "exploding chest" pictogram is required for compounds with systemic toxicity. The tablet binding compositions provided herein contain no ingredient that results in systemic toxicity and thus will avoid the new OSHA GHS "exploding chest" pictogram. The tablet binding compositions provided herein could be approved by the US EPA Design for the Environment (DfE) group to allow products containing the tablet binding compositions provided herein to be branded with their logo. Achieving an approval from the DfE is not possible with compositions containing boric acid.

The acetate salts of the tablet binding compositions provided herein generally are selected to be in an anhydrous form, such as an anhydrous crystalline or powder form. Any anhydrous acetate salt can be used in the tablet binding compositions provided herein. Although hydrated crystalline forms of the acetate salt can be used, the water of hydration of the salt could migrate through the finished tablet, which could negatively impact shelf life of the tablet. In addition, the hydrated forms of some of the acetate salts are hygroscopic, which can negatively impact tablet formation and/or stability.

In some applications, a water soluble acetate salt is preferred. The acetate salt can be a water soluble acetate salt in anhydrous form. In some applications, the acetate is an anhydrous salt of an alkali metal. Preferred among these are the anhydrous sodium acetate salts and potassium acetate salts. In some applications, the acetate is an anhydrous salt of an alkaline earth metal. Preferred among these are the anhydrous calcium acetate salts and magnesium acetate salts. In some applications, the acetate is an anhydrous salt of a transition metal (an IUPAC Group 11 metal or a CAS Group Number 1B metal). Preferred among these are the anhydrous silver acetate salts and copper acetate salts. In some applications, the anhydrous acetate salt of the tablet binding composition is selected from among sodium acetate, potassium acetate, calcium acetate, magnesium acetate, silver acetate and combinations thereof. Acetate salts, including anhydrous forms of acetate salts, are commercially available (e.g., from Niacet Corporation, Niagara Falls, N.Y.; Chem One Ltd., Houston, Tex., USA; Vasa Pharmachem Pvt. Ltd., Gujarat, India; and J&K Scientific GmbH, Pforzheim, Germany).

The ground particles or crystals of the anhydrous acetate salt generally are available in different particle sizes. In some applications, the acetate selected for the tablet binding compositions provided herein have a particle size distribution in the range of from about 100 μm to about 1200 μm. In some applications, the acetate selected for the tablet binding compositions provided herein have a particle size distribution in the range of from about 50 μm to about 500 μm, or in the range of from about 100 μm to about 1000 μm, or in the range of from about 150 μm to about 950 μm. In some applications, the acetate salt has a particle size greater than 50 μm, or greater than 100 μm, or greater than 150 μm, or greater than 200 μm, or greater than 250 μm, or greater than 300 μm, or greater than 350 μm, or greater than 400 μm, or greater than 450 μm, or greater than 500 μm, or greater than 550 μm, or greater than 600 μm, or greater than 650 μm, or greater than 700 μm, or greater than 750 μm, or greater than 800 μm, or greater than 850 μm, or greater than 900 μm, or greater than 950 μm, or greater than 1000 μm. In some applications, at least 70% of the particles of the acetate salt are greater than 150 μm. In some applications, at least 50% of the particles of the acetate salt are greater than 250 μm.

In some applications, the acetate salt has a particle size such that at least 90% passes through a U.S. Standard Mesh No. 20 sieve. In some applications, the acetate salt has a particle size such that at least 80% passes through a U.S. Standard Mesh No. 30 sieve. In some applications, the acetate salt has a particle size such that at least 70% passes through a U.S. Standard Mesh No. 20 sieve. In some applications, the acetate salt has a particle size such that at least 60% passes through a U.S. Standard Mesh No. 30 sieve. In some applications, the acetate salt has a particle size such that at least 10% passes through a U.S. Standard Mesh No. 30 sieve. In some applications, the acetate salt has a particle size such that at least 60% passes through a U.S. Standard Mesh No. 30 sieve. In some applications, the acetate salt has a particle size such that at least 50% is retained on a U.S. Standard Mesh No. 40 sieve. In some applications, acetate salt has a particle size such that at least 70% is retained on a U.S. Standard Mesh No. 60 sieve. In some applications, the acetate salt has a particle size such that at least 80% is retained on a U.S. Standard Mesh No. 100 sieve.

The acetate salt can be present in the tablet binding compositions provided herein in an amount that is from at or about 15% to at or about 85% by weight of the composition. The acetate salt can be present in the tablet binding compositions provided herein in an amount that is from at or about 20% to at or about 80% by weight of the composition. In some applications, the acetate salt is present in an amount that is selected from among at least 15%, at least 20%, at least 25%, at least 30%, at least 35%, at least 40%, at least 45%, at least 50%, at least 55%, at least 60%, at least 65%, at least 70%, at least 75%, and at least 80% based on the weight of the composition. With respect to the C6 saccharide derivative sequestrant component of the tablet binding compositions provided herein, the acetate salt can be present in a ratio of from about 1:5 acetate:sequestrant to about 5:1 acetate:sequestrant. For example, the ratio of acetate:sequestrant can be selected from among 1:5, 1:4.75, 1:4.5, 1:4.25, 1:4, 1:3.75, 1:3.5, 1:3.25, 1:3, 1:2.75, 1:2.5, 1:3.25, 1:2, 1:1.75, 1:1.5, 1:1.25, 1:1, 1:1.25, 1:1.5, 1:1.75, 1:2, 1:2.25, 1:2.5, 1:2.75, 1:3, 1:3.25, 1:3.5, 1:3.75, 1:4, 1:4.25, 1:4.5, 1:4.75 and 1:5.

In some applications, the tablet binding compositions provided herein contain one or more of sodium acetate, potassium acetate, calcium acetate, magnesium acetate or silver acetate, in combination with one or more of fucosamine, glucosamine, galactosamine, mannosamine, allitol, altritol, fucitol, galactitol, glucitol, iditol, mannitol, allonic acid, altronic acid, fuconic acid, galactonic acid, gluconic acid, gulonic acid, idonic acid, mannonic acid, sorbonic acid, talonic acid, potassium allonate, potassium altronate, potassium fuconate, potassium galactonate, potassium gluconate, potassium gulonate, potassium idonate, potassium mannonate, potassium sorbonate, potassium talonate, sodium allonate, sodium altronate, sodium fuconate, sodium galactonate, sodium gluconate, sodium gulonate, sodium idonate, sodium mannonate, sodium sorbonate, sodium talonate, allonolactone, altronolactone, gluconolactone, mannolactone, gulonolactone, idonolactone, galactonolactone, talonolactone, glucono-delta-lactone, glucaric acid, galactaric acid, mannaric acid, potassium glucarate, or sodium glucarate.

C. METHODS FOR PREPARING THE TABLET BINDING COMPOSITIONS

The tablet binding compositions provided herein can be prepared by blending together the acetate salt and the C6 saccharide derivative sequestrant to form a mixture in which the powders are evenly distributed and homogeneous. Any powder blending technique that results in a uniform final product can be used. Known devices, such as a Hobart® planetary mixer, a vee-blender, a vee-cone blender, a rotary batch mixer, a fluidized bed mixer, a ribbon blender, a paddle blender and a plow blender or combinations thereof, can be used to mix the components. The mixing can be carried out at room temperature (about 21° C. or 70° F.) under atmospheric pressure, and is not adversely affected by temperature or pressure conditions. High humidity has a negative impact on the blending. A dehumidification system is used in the blending area to maintain a relative humidity of about 25% or less, or 15% or less. Any dehumidification system known in the art can be used to control humidity (e.g., any of the dehumidification systems available from Munters AB, Kista, Sweden). The amount of time required to form a uniform blend can depend on the amount of material to be blended and the size and type of mixing equipment selected. The tablet binding compositions are not adversely affected by the time of mixing. In some applications, a vee-cone blender large enough so that no more than 50% of its capacity is used to contain the components is used to mix the components for 1 hour to obtain a uniform mixture.

D. TABLETS CONTAINING THE TABLET BINDING COMPOSITIONS

The tablet binding compositions provided herein can be used to bind the components of a cleaning or disinfectant composition to form a tablet. The tablet binding compositions provided herein bind the components of the formulation during compression and release the formed tablet from the press mold without breaking, sticking or picking. The tablet can include up to about 25% tablet binding compositions provided herein based on the total weight of the tablet. In some applications, the tablet contains from about 0.5% to about 25% tablet binding compositions provided herein. In some applications, the amount of the tablet binding compositions provided herein present in the tablet, based on the total weight of the tablet, is from about 1% to about 20%, or about 2% to about 18%, or about 3% to about 17%, or about 4% to about 16%, or about 5% to about 15%. In some applications, the amount of the tablet binding compositions provided herein present in the tablet, based on the total weight of the tablet, is at least about 1%, or at least about 2.5%, or at least about 5%, or at least about 6%, or at least about 7%, or at least about 8%, or at least about 9%, or at least about 10%, or at least about 11%, or at least about 12%, or at least about 13%, or at least about 14%, or at least about 15%, and up to about 25% of the total weight of the tablet.

The tablet can be of any geometric shape. Exemplary shapes include spherical, cube, disk, rod, triangular, square, rectangular, pentagonal, hexagonal, lozenge, modified ball, core rod type (with hole in center), capsule, oval, bullet, arrowhead, compound cup, arc triangle, arc square (pillow), diamond, half-moon and almond. The tablets can be convex or concave. The tablets can be flat-faced plain, flat-faced bevel-edged, flat-faced radius edged, concave bevel-edged or any combination thereof. In some applications, the tablet can have a generally axially-symmetric form and can have a round, square or rectangular cross-section. The tablet can be of uniform composition, or can contain two or more distinct regions having differing compositions. In some applications, the tablets contain no boric acid, borates or perborates.

Surfactants

The cleaning or disinfecting formulation to be provided in tablet form can and generally do contain a surfactant. The surfactant can be a water-soluble or water-dispersible nonionic, semi-polar nonionic, anionic, cationic, amphoteric, or zwitterionic surfactant or a combination thereof. Examples of suitable surfactants are described, e.g., at col. 9, line 64 through col. 14, line 25 of U.S. Pat. No. 8,551,932 B2, and at col. 9, line 48 through col. 14, line 25 of U.S. Pat. No. 8,454,709 B2, the disclosure of each of which is incorporated herein. In some applications, the formulation includes a combination of surfactants. The formulation can contain a nonionic surfactant in combination with one or more of an anionic, cationic, amphoteric, or zwitterionic surfactant. The formulation can contain a nonionic surfactant and an anionic surfactant in combination with one or more of a cationic, amphoteric, or zwitterionic surfactant. The formulation can contain a nonionic surfactant and cationic surfactant in combination with one or more of an anionic, amphoteric, or zwitterionic surfactant. The formulation can include an alcohol ethoxylate alone or in combination with one or more of a water-soluble or water-dispersible nonionic, semi-polar nonionic, anionic, cationic, amphoteric, or zwitterionic surfactant. The formulation can include an sodium dodecylbenzene sulfonate alone or in combination with one or more of a water-soluble or water-dispersible nonionic, semi-polar nonionic, anionic, cationic, amphoteric, or zwitterionic surfactant. In some applications, the surfactant is a non-ionic surfactant that contains an alcohol ethoxylate or an alcohol ethoxysulfate or a combination thereof. When present, the surfactant can be present in an amount from about 0.1% to about 50%, or from about 0.25% to about 30%, or from about 0.5% to about 20%, or from about 0.5% to about 10%, based on the total weight of the formulation. In some applications, the surfactant is present in an amount that is at least 0.5%, or at least 1%, or at least 5%, or at least 10%, or at least 15%, or at least 20%, or at least 25%, or at least 30%, or at least 35%, or at least 40%, or at least 45%, or at least 50%, based on the total weight of the tablet composition.

Excipients

The cleaning or disinfecting formulation to be combined with the tablet binding composition provided herein to be formed into a tablet can include excipients. The excipients can include diluents, glidants (flow aids) and disintegrants to ensure efficient tableting, disintegrants to promote tablet break-up, and pigments or colorants to make the tablets visually attractive. Diluents are inert ingredients sometimes used as bulking agents in order to decrease the concentration of the active ingredient in the final formulation. Glidants can be added to improve the powder flow. They typically are used to help the component mixture to fill the die evenly and uniformly prior to compression. Disintegrants can be added to formulations in order to help the tablets disintegrate when they are placed in a liquid environment and so release the active ingredient. If present, an excipient can be present in an amount of up to 60% by weight of the total tablet weight. In some applications, an excipient can be included in the formulation in an amount of about 0.05% to about 50%, or from about 0.5% to about 40%, or from about 1% to about 30%, or from about 5% to about 25%, based on the total weight of the tablet.

Other Ingredients

The tablet formulation can contain other ingredients. For example, in some applications, a fragrance can be included in the formulation to enhance consumer appeal. A fragrance can be included in amounts up to about 25% by weight of the total composition, usually in amounts in the range of about 0.01% to about 10%. Suitable fragrances include any that does not interact with any component of the formulation, and can include hydrocarbons, alcohols, aldehydes, ketones, esters, ethers, and combinations thereof. The fragrances can be encapsulated to isolate the fragrance until the time of use of the tablet. Exemplary fragrances are described in U.S. Pat. No. 6,849,591 (Boeckh et al) at col. 3, line 17 through col. 4, line 12, and U.S. Pat. No. 4,515,705 (Moeddel) at col. 3, lines 9-68, each of which is incorporated herein by reference. Fragrances are commercially available from a number of suppliers (e.g., International Flavors & Fragrances Inc., New York, N.Y., USA; Givaudan SA, Cincinnati, Ohio, USA; and Takasago International Corporation, Rockleigh, N.J., USA).

The cleaning or disinfecting formulation to be combined with the tablet binding composition provided herein to be formed into a tablet also can include other ingredients, such as enzymes, including lipases, proteases, cellulases and/or amylases, bleaches or bleaching agents, sodium percarbonate or similar materials, bleach activators, acids, foam boosters, carbonates or bicarbonates, phosphates, anti-microbial agents, wetting agents, dispersing agents, hydrotropes, polymers, rheology control agents, chelating agents, pH modifiers, foam suppressants, anti-corrosion agents and other functional additives. In some applications, the formulation includes an expanded percarbonate as described in U.S. Pat. Appln. Pub. No. US2012/0219513. In some applications, the formulation can include a sodium perborate or an expanded sodium perborate. In some applications, the cleaning or disinfecting formulation contains an acid selected from among acetic, adipic, azelaic, citric, fumaric, glutaric, maleic, malonic, oxalic, pimelic, suberic, sebacic, and succinic acid and combinations thereof. In some applications, the acid is selected from among acetic acid, citric acid, malic acid, adipic acid and oxalic acid. In some applications, the formulation includes a solid acetic acid as described in U.S. Pat. Appln. Pub. No. US2012/0208740. These other ingredients can be present in the range of about 0.05% to 75%, or in the range of about 0.25% to 60%, or in the range of about 0.5% to 50%, or in the range of about 0.75% to 40% based on the weight of the tablet. In some applications, the tablet includes ingredients that allow the tablet to effervesce.

In some applications, the cleaning or disinfecting formulation contains a phosphate selected from among sodium acid pyrophosphate, monosodium phosphate, disodium phosphate, and sodium dihydrogen orthophosphate. In some applications, the cleaning or disinfecting formulation contains a foam booster selected from among fatty acid amides, alkoxylated fatty acid amides, fatty acid amides of alkanolamines, fatty acid amides of alkoxylated alkanolamines, and fatty acid amides of alkanolamide esters and combinations thereof. When present, a phosphate or foam booster can be present in the range of about 0.05% to 75%, or in the range of about 0.15% to 60%, or in the range of about 0.25% to 50%, or in the range of about 0.5% to 40% based on the weight of the tablet.

In some applications, the cleaning or disinfecting formulation includes sodium percarbonate, alone or in combination with a bleach activator. Examples of bleach activators are described in U.S. Pat. No. 4,915,854 (Mao et al.) at col. 24, line 6 through col. 26, line 60; and U.S. Pat. No. 4,634,551 (Burns et al.) at col. 3, line 25 through col. 5, lines 26, the disclosure of each of which is incorporated by reference herein. Typical activators include decanoyloxybenzenecarboxylic acid (DOBA), nonanoyloxybenzene sulfonate (NOBS) and tetraacetylethylenediamine (TAED). In some applications, the cleaning or disinfecting formulation includes sodium percarbonate and tetraacetyl-ethylenediamine (TAED). When present, a bleach activator can be present in an amount of from about 0.05% to about 50%, or in an amount of from about 0.1% to 40%, based on the total weight of the formulation.

In some applications, the cleaning or disinfecting formulation includes a bleaching agent, such as a percarboxylic acid bleaching agent. Examples include calcium peroxide, magnesium peroxide, diperoxy-dodecanedioic acid, magnesium monoperoxyphthalate hexahydrate, nonyl amino-6-oxoperoxysuccinic acid and the magnesium salt of meta-chloroperbenzoic acid. The formulations can include a peroxygen bleaching agent. Examples of peroxygen bleaching agents include urea peroxide and the alkali metal percarbonates and perphosphates, such as sodium percarbonate monohydrate, sodium carbonate peroxyhydrate, and sodium pyrophosphate peroxyhydrate. When present, a bleaching agent can be present in an amount of from about 0.05% to about 50%, or in an amount of from about 0.1% to 40%, based on the total weight of the formulation.

In some applications, the cleaning or disinfecting formulation includes a liquid component. The liquid component can be selected from among water, alcohols, glycols, polyglycols, glycol ethers, propanediols, glycerin, esters, terpenes, anionic surfactants, amphoteric surfactants, cationic surfactants, nonionic surfactants, zwitterionic surfactants, and combinations thereof. When present, a liquid component can be present in an amount up to 10% of the total weight of the tablet. In some applications, the liquid component can present in an amount up to 5% of the total weight of the tablet. In some applications, the liquid component can present in an amount of from about 0.1% to about 10%, or 0.5% to about 7.5%, or about 1% to about 5% of the total weight of the tablet. When present, the liquid component can be incorporated in a conventional manner into the solid particulate components of the tablet binding composition.

A polymer coating can be applied to the surface of the tablet to make the tablet smoother and to make it more resistant to the environment (extending its shelf life) or to enhance the tablet's appearance. Any polymer coating known in the art can be used. Suitable coating materials can include adipic acid, azelaic acid, glutaric acid, malonic acid, oxalic acid, pimelic acid, sebacic acid, suberic acid, succinic acid, undecanedioic acid, dodecanedioic acid, tridecanedioic acid, hydroxypropyl cellulose, hydroxypropyl methylcellulose (e.g., Opadry® coating), polyvinylacetate, hydroxyethyl cellulose, methylhydroxyethyl cellulose, methyl cellulose, ethyl cellulose (e.g., Surelease® coating), cellulose acetate, sodium carboxymethyl cellulose, polymers and copolymers of acrylic acid and methacrylic acid and esters thereof (e.g., Eudragit® RL, Eudragit® RS, Eudragit® L100, Eudragit® 5100, Eudragit® NE), or polyvinylpyrrolidone or combinations thereof Dissolution of the Tablets The cleaning or disinfecting tablets containing the tablet binding compositions provided herein can be dissolved to produce a solution that can be used to treat and/or clean hard surfaces. The tablets can be dissolved in any appropriate solvent. In some applications, the solvent is or comprises water. The water can be purified water. Dissolution can be achieved using any appropriate method to agitate the solvent to facilitate dissolution of the tablet, such as low shear or high shear mixing, stirring, blending, inverting the container, and shaking the container and combinations thereof. Dissolution of the tablets in the solvent results in a cleaning or disinfecting solution. One or more tablets can be used to modulate the final concentration of the resulting cleaning or disinfecting solution. Tablets of different formulations can be combined to yield a solution of mixed functionality.

The resulting cleaning or disinfecting solution can be used on any hard surface, such as the surfaces of items in kitchens and bathrooms, cars and other automotive vehicles, planes, boats, watercraft, and campers, and the surfaces of utensils, glassware, windows, and appliances, e.g., refrigerators, freezers, garbage disposals, washing machines, dryers, ovens, microwave ovens and dishwashers. The hard surfaces can be inclined or vertical. Such hard surfaces can be found in private households as well as in commercial, institutional and industrial environments. The hard surfaces can be made of or contain any number of different materials, e.g., enamel, ceramic, glass, stainless steel, chrome, vinyl, linoleum, melamine, glass, fiberglass, Formica®, granite, marble, hardwood, grout, porcelin, concrete, plastic, plastified wood, metal or any painted or varnished or sealed surface. Examples of hard surfaces include plate ware, crockery, flatware, cutlery, glassware, utensils, floors, walls, tiles, windows, doors, cupboards, sinks, counter tops, bathtubs, showers, shower stalls, shower doors, plastic shower curtains, wash basins, toilets, toilet seats, fixtures and fittings, mirrors, lavatory pans, urinals, drains, appliance surfaces, dash boards, decks, tire rims, door handles, hand rails, phones, computer keyboards, and work surfaces including cutting and chopping boards.

Application Methods

The solutions prepared by dissolving the tablets containing the tablet binding compositions provided herein can be applied to surfaces by any technique or method known in the art. Exemplary application methods include spraying, wiping, direct application, immersion, or as part of a normal cleaning process, such as part of a laundry washing or dishwashing process. The solution can be applied directly to a surface as a spray or fine mist, via a woven or nonwoven substrate, brush, sponge, wipe or cleaning pad, or any combination thereof.

Articles of Manufacture

The cleaning or disinfectant compositions in the form of a tablet containing the tablet binding composition provided herein can be part of an article of manufacture, which can include a container suitable for containing the tablets, such as for shipping and/or storage. The tablets containing the tablet binding composition provided herein can be stored or shipped in a variety of containers, and the containers can be made of or contain any of a variety of container materials, such as glass, acrylonitrile butadiene styrene (ABS), high impact polystyrene, polycarbonate, high density polyethylene, low density polyethylene, high density polypropylene, low density polypropylene, polyethylene terephthalate, polyethylene terephthalate glycol and polyvinylchloride and combinations thereof. The containers can include barrier films to increase storage stability. Suitable barrier films can include nylons, polyethylene terephthalate, fluorinated polyethylenes, and copolymers of acrylonitrile and methylmethacrylate.

An article of manufacture can include tablets containing the tablet binding composition provided herein and a set of instructions, such as for the use of the tablets. In some applications, the article of manufacture includes instructions for preparing a cleaning/disinfectant solution by dissolving the tablets in an appropriate solvent. The article of manufacture can include tablets containing the tablet binding composition provided herein and storage instructions, or a material safety data sheet or a combination thereof. The article of manufacture can include tablets containing the tablet binding composition provided herein and a dispenser or applicator for preparing or for use with the cleaning or disinfectant solution prepared by dissolution of the tablets, alone or in combination of any of storage instructions, preparation instructions or a material safety data sheet. The tablets in any of the articles of manufacture can include a dissolvable film for encasing the tablets, such as a film prepared from polyvinyl alcohol. The tablets in any of the articles of manufacture can include a polymer coating.

E. METHODS FOR PREPARING TABLETS

Tablets containing the tablet binding composition provided herein can be prepared using any method known in the art, including compression, casting, briquetting, injection molding and extrusion. In some applications, the tablet preferably is produced by compression, for example in a tablet press.

Direct compression often is considered to be the simplest and the most economical process for producing tablets. Direct compression requires only two principal steps: the mixing of all the ingredients and compressing this mixture into a tablet. Any method known in the art for formation of a tablet can be used to prepare a tablet containing the tablet binding compositions provided herein. For example, a cleaning formulation in tablet form can be prepared by admixing the components of the cleaning formulation with the tablet binding composition provided herein to achieve a uniform mix. Any powder blending, mixing or shaking technique that results in a uniform final product can be used. Known devices, such as a Hobart® planetary mixer, a vee-blender, a vee-cone blender, a rotary batch mixer, a fluidized bed mixer, a ribbon blender, a paddle blender and a plow blender or combinations thereof, can be used to mix the components. The resulting uniform mix then is placed into a die of the desired geometry in a conventional tablet press, such as a single stroke or rotary press. The press includes a punch suitably shaped for forming the tablet. The uniform mix is then subjected to a compression force sufficient to produce a tablet, and a tablet containing the tablet binding composition provided herein is ejected from the tablet press.

Any tableting equipment known in the art can be used for tablet formation. Suitable equipment includes a standard single stroke or a rotary press. Such presses are commercially available, and are available from, e.g., Carver, Inc. (Wabash, Ind.), Compression Components & Service, LLC (Warrington, Pa.), Specialty Measurements Inc. (Lebanon, N.J.), GEA Pharma Systems (Wommelgem, Belgium), Korsch America Inc. (South Easton, Mass.) or Bosch Packaging Technology (Minneapolis, Minn.).

The tablets containing the tablet binding composition provided herein can have any desired diameter, such as a diameter of between about 5 mm and about 75 mm. In some applications, the tablets have a diameter of at least 6 mm, at least 7 mm, at least 8 mm, at least 9 mm, at least 10 mm, at least 15 mm, at least 20 mm, at least 25 mm, at least 30 mm, at least 35 mm, at least 40 mm, at least 45 mm, at least 50 mm, at least 55 mm, at least 60 mm or at least 70 mm. The tablets containing a tablet binding composition provided herein can be of any weight, such as a weight between 100 mg and 100 g.

The tableting can be carried out at room temperature (21° C. or 70° F.) under atmospheric pressure, and is not adversely affected by temperature or pressure conditions. High humidity has a negative impact on tableting. A dehumidification system is used in the tableting area to maintain a relative humidity of about 25% or less, or 15% or less. Any dehumidification system known in the art can be used to control humidity (e.g., any of the dehumidification systems available from Munters AB, Kista, Sweden).

The tablet can be compressed by applying a compression pressure of at least about 1500 PSI, preferably at least 1750 PSI. In some applications, the tablet is compressed applying a compression pressure of at least 2000 PSI, or at least 2500 PSI, or at least 5000 PSI, or at least 7500 PSI, or at least 10,000 PSI. In some applications, the tablet is compressed applying a compression pressure from about 1750 PSI to about 20,000 PSI. In some applications, the tablet is compressed applying a compression pressure in the range of about 1750 PSI to about 15,000 PSI, or from about 1800 PSI to about 14,000 PSI, or from about 1850 PSI to about 12,500 PSI, or from about 1900 PSI to about 10,000 PSI, or from about 2000 PSI to about 9500 PSI, or from about 1750 PSI to about 8500 PSI, or from about 1750 PSI to about 7500 PSI, or from about 1750 PSI to about 5500 PSI. The compression pressure can be selected to most economically provide optimum tablet integrity and strength (measured, e.g., by tablet hardness, where the tablet industry generally considers optimal operating range for tablet hardness to be between 9 kPa and the 23 kPa) and having the desired product aesthetics and dissolution characteristics. In some applications, the tablet is compressed applying a compression pressure that yields a tablet having a tablet hardness between about 9 kPa and about 23 kPa. In some applications, the tablet is compressed applying a compression pressure that yields a tablet having a tablet hardness between about 10 kPa and about 20 kPa. In some applications, the tablet is compressed applying a compression pressure that yields a tablet having a tablet hardness of at least 10 kPa. The tablets containing the tablet binding compositions provided herein exhibit no tablet face sticking or die wall streaking during manufacture, and exhibit smooth face surfaces, good edges and good side walls with few defects, and have low weight loss.

F. TEST METHODS

Visual Appearance of Tablets

Visual inspection of the tablet production process can identify problem formulations or inferior process conditions or both. During production of the tablets, the tablet die is observed to determine how well the tablets are released from the die. The tablets should eject smoothly from the die without sticking (e.g., tablet face sticking) and without leaving any material on the die (e.g. die wall streaking), and should exhibit smooth face surface, good edges and good side walls with no or few visually detactable defects. In cases of failing formulations, tablets can become stuck in the die, or the tablets fail to retain their shape, or the tablets delaminate or have defects on a face or side walls or both, or do not product good edges.

Tablet Weight Loss

Tablets that lose more than 0.5% of their original weight are indicative of tablets with poor tablet qualities like rough edges, die wall streaking and tablet face sticking. The amount of tablet weight loss during the manufacturing process can be measured using any teachnique known in the art. As an exemplary method, the initial amount of material added to the die is recorded, and after the tablet is made via compression, the tablet is weighed. The difference between the weight of the tablet and the initial amount of material added to the tablet die is the "weight loss" value. Tablets that exhibit a weight loss of more than 0.5% are deemed to exhibit poor tablet qualities.

Tablet Hardness

Tableting is performed at a compression pressure determined optimal to provide a cohesive tablet that has a desired dissolution profile. If the tabletting process is performed lower than this compression pressure, cracks and defects will be present in the tablets, or the tablets will exhibit insufficient cohesion and will crumble when ejected from the die. If tableting is performed at a pressure exceeding the optimal pressure, tablet hardness will be higher than necessary, resulting in a tablet that can fail to quickly disintegrate or dissolve. Tablet hardness can be measured using any teachnique or aparatus known in the art for testing tablet hardness. For example, a force gauge can be used to determine breaking force, which is indicative of the strength of the tablet. Exemplary of the guages that can be used to measure tablet strength are the guages available from Imada, Inc. (Northbrrok, Ill., USA, such as the models MPS and MPSH), the VK 200 tablet hardness tester available from Agilent Technologies, Inc. (Englewood, Colo., USA) and the MultiTest 50 tablet hardness tester available from SOTAX Corporation (Westborough, Mass., USA).

Tablet Friability

The friability of a tablet is a measure of the loss of weight suffered by a tablet due to abrasion or shock. Friability can be measured using any method known in the art. For example, friability can be measured by allowing test tablets to roll and fall within a rotating apparatus known as a friabilator. The abrasion caused by a tumbling action is comparable to tablets rubbing against each other or being shaken against the walls of their container in general use, and to a shock resulting from a fall, such as might be encountered during various steps in packaging, handling and transport. The tablets can have a friability of about 10% or less, about 5% or less, about 3% or less, or about 1% or less.

Solution Clarity

The clarity of the solution resulting from dissolution of the cleaner/disinfectant tablets containing the tablet binding composition provided herein can be an important aesthetic characteristic to many consumers. The qualitative clarity of a solution can be determined visually, such as by visual comparison to a distilled water control solution. A solution can be rated accordingly to the ability to see light transmitted through the solution. A solution with no or little suspended particulate matter, indicating good dissolution of the tablet and its components, generally exhibits a clear solution. A solution with a small amount of particulate matter suspended therein generally exhibits a hazy solution. A solution with a large amount of suspended particulates exhibits a cloudy solution. An exemplary test method includes dissolving the tablet in a given amount of solvent. For example, a 1 gram tablet can be dissolved in 100 mL of deionized water using 140 mL glass beakers and observations can be made regarding solution clarity. Solutions can range from "clear" to "cloudy."

The clarity of a solution can be quantified using any method known in the art. For example, a turbidimeter can be used. The turbidimeter measures the amount of suspended solids in a solution. For this test, a cuvette of the turbidimeter is completely filled by the test sample, the cuvette is placed in the instrument (e.g., a DRT 100B turbidimeter available from HF Scientific, Fort Myers, Fla.) and the displayed reading, in nephelometric turbidity units, is recorded. Alternatively, the clarity of a solution can be determined through a measurement of the color, reflectance, absorbance or transmittance (or any combination thereof) of the solution. For example, sample clarity can be quantified as a percentage of transmittance at 420 nm using a colorimeter (e.g., a Libra S2 colorimeter, Biochrom US, Holliston, Mass., USA). For this test, a cuvette of the calorimeter is completely filled by the test sample, the cuvette is placed in the instrument and the transmittance is recorded. A comparison to a deionized water control can be used to prepare a correlation curve.

G. EXAMPLES

The following examples illustrate specific aspects of the present invention and are not intended to limit the scope thereof in any respect and should not be so construed.

Example 1

Preparation of Tablet Binding Compositions Containing an Acetate Salt and a C6 Saccharide Derivative Sequestrant Tablet binding compositions provided herein containing an acetate salt and a C6 saccharide derivative sequestrant were prepared. The formulation for each of the tablet binding compositions is provided in Table 1. The tablet binding compositions provided herein have a ratio of acetate:C6 saccharide derivative sequestrant in the range of from about 5:1 to about 1:5. To prepare each tablet binding composition, each of the indicated amounts of the acetate salt and the C6 saccharide derivative sequestrant was placed in a 16 oz. Mason jar. The lid to the jar was secured in place and the jar was shaken by hand for at least one minute to achieve a homogeneous blend.

TABLE 1

Formulations of Tablet Binding Compositions.

| | Acetate | wt. (g) | Sequestrant | wt. (g) | Ratio |
|---|---|---|---|---|---|
| Example 1-A1 | Sodium acetate, anhydrous [1] | 80 | d-Glucitol, anhydrous [2] | 20 | 4:1 |
| Example 1-A2 | Sodium acetate, anhydrous [1] | 20 | d-Glucitol, anhydrous [2] | 80 | 1:4 |
| Example 1-A3 | Sodium acetate, anhydrous [1] | 60 | d-Glucitol, anhydrous [2] | 40 | 3:2 |
| Example 1-A4 | Sodium acetate, anhydrous [1] | 40 | d-Glucitol, anhydrous [2] | 60 | 2:3 |
| Example 1-A5 | Sodium acetate, anhydrous [1] | 50 | d-Glucitol, anhydrous [2] | 50 | 1:1 |
| Example 1-A6 | Sodium acetate, anhydrous [1] | 83.33 | d-Glucitol, anhydrous [2] | 16.67 | 5:1 |
| Example 1-A7 | Sodium acetate, anhydrous [1] | 16.67 | d-Glucitol, anhydrous [2] | 83.33 | 1:5 |
| Example 1-B1 | Sodium acetate, anhydrous [1] | 80 | Glucono-delta-lactone, anhydrous [3] | 20 | 4:1 |
| Example 1-B2 | Sodium acetate, anhydrous [1] | 20 | Glucono-delta-lactone, anhydrous [3] | 80 | 1:4 |
| Example 1-B3 | Sodium acetate, anhydrous [1] | 60 | Glucono-delta-lactone, anhydrous [3] | 40 | 3:2 |
| Example 1-B4 | Sodium acetate, anhydrous [1] | 40 | Glucono-delta-lactone, anhydrous [3] | 60 | 2:3 |
| Example 1-B5 | Sodium acetate, anhydrous [1] | 50 | Glucono-delta-lactone, anhydrous [3] | 50 | 1:1 |
| Example 1-B6 | Sodium acetate, anhydrous [1] | 83.33 | Glucono-delta-lactone, anhydrous [3] | 16.67 | 5:1 |
| Example 1-B7 | Sodium acetate, anhydrous [1] | 16.67 | Glucono-delta-lactone, anhydrous [3] | 83.33 | 1:5 |
| Example 1-C1 | Sodium acetate, anhydrous [1] | 80 | Sodium gluconate, anhydrous [4] | 20 | 4:1 |
| Example 1-C2 | Sodium acetate, anhydrous [1] | 20 | Sodium gluconate, anhydrous [4] | 80 | 1:4 |
| Example 1-C3 | Sodium acetate, anhydrous [1] | 60 | Sodium gluconate, anhydrous [4] | 40 | 3:2 |
| Example 1-C4 | Sodium acetate, anhydrous [1] | 40 | Sodium gluconate, anhydrous [4] | 60 | 2:3 |
| Example 1-C5 | Sodium acetate, anhydrous [1] | 28.57 | Sodium gluconate, anhydrous [4] | 71.43 | 2.5:1 |
| Example 1-C6 | Sodium acetate, anhydrous [1] | 71.43 | Sodium gluconate, anhydrous [4] | 28.57 | 1:2.5 |
| Example 1-C7 | Sodium acetate, anhydrous [1] | 50 | Sodium gluconate, anhydrous [4] | 50 | 1:1 |
| Example 1-C8 | Sodium acetate, anhydrous [1] | 83.33 | Sodium gluconate, anhydrous [4] | 16.67 | 5:1 |
| Example 1-C9 | Sodium acetate, anhydrous [1] | 16.67 | Sodium gluconate, anhydrous [4] | 83.33 | 1:5 |
| Example 1-D1 | Potassium acetate, anhydrous [5] | 80 | d-Glucitol, anhydrous [2] | 20 | 4:1 |
| Example 1-D2 | Potassium acetate, anhydrous [5] | 20 | d-Glucitol, anhydrous [2] | 80 | 1:4 |

TABLE 1-continued

Formulations of Tablet Binding Compositions.

| | Acetate | wt. (g) | Sequestrant | wt. (g) | Ratio |
|---|---|---|---|---|---|
| Example 1-E1 | Potassium acetate, anhydrous [5] | 80 | Glucono-delta-lactone, anhydrous [3] | 20 | 4:1 |
| Example 1-E2 | Potassium acetate, anhydrous [5] | 20 | Glucono-delta-lactone, anhydrous [3] | 80 | 1:4 |
| Example 1-F1 | Potassium acetate, anhydrous [5] | 80 | Sodium gluconate, anhydrous [4] | 20 | 4:1 |
| Example 1-F2 | Potassium acetate, anhydrous [5] | 20 | Sodium gluconate, anhydrous [4] | 80 | 1:4 |
| Example 1-G1 | Calcium acetate, anhydrous [6] | 80 | d-Glucitol, anhydrous [2] | 20 | 4:1 |
| Example 1-G2 | Calcium acetate, anhydrous [6] | 20 | d-Glucitol, anhydrous [2] | 80 | 1:4 |
| Example 1-H1 | Calcium acetate, anhydrous [6] | 80 | Glucono-delta-lactone, anhydrous [3] | 20 | 4:1 |
| Example 1-H2 | Calcium acetate, anhydrous [6] | 20 | Glucono-delta-lactone, anhydrous [3] | 80 | 1:4 |
| Example 1-I1 | Calcium acetate, anhydrous [6] | 80 | Sodium gluconate, anhydrous [4] | 20 | 4:1 |
| Example 1-I2 | Calcium acetate, anhydrous [6] | 20 | Sodium gluconate, anhydrous [4] | 80 | 1:4 |
| Example 1-J1 | Magnesium acetate, anhydrous [7] | 80 | d-Glucitol, anhydrous [2] | 20 | 4:1 |
| Example 1-J2 | Magnesium acetate, anhydrous [7] | 20 | d-Glucitol, anhydrous [2] | 80 | 1:4 |
| Example 1-K1 | Magnesium acetate, anhydrous [7] | 80 | Glucono-delta-lactone, anhydrous [3] | 20 | 4:1 |
| Example 1-K2 | Magnesium acetate, anhydrous [7] | 20 | Glucono-delta-lactone, anhydrous [3] | 80 | 1:4 |
| Example 1-L1 | Magnesium acetate, anhydrous [7] | 80 | Sodium gluconate, anhydrous [4] | 20 | 4:1 |
| Example 1-L2 | Magnesium acetate, anhydrous [7] | 20 | Sodium gluconate, anhydrous [4] | 80 | 1:4 |
| Example 1-M1 | Sodium acetate, anhydrous [1] | 80 | Glucosamine hydrochloride [8] | 20 | 4:1 |
| Example 1-M2 | Sodium acetate, anhydrous [1] | 20 | Glucosamine hydrochloride [8] | 80 | 1:4 |
| Example 1-N1 | Sodium acetate, anhydrous [1] | 80 | d-Mannitol [9] | 20 | 4:1 |
| Example 1-N2 | Sodium acetate, anhydrous [1] | 20 | d-Mannitol [9] | 80 | 1:4 |
| Example 1-O1 | Sodium acetate, anhydrous [1] | 80 | Potassium gluconate, anhydrous [10] | 20 | 4:1 |
| Example 1-O2 | Sodium acetate, anhydrous [1] | 20 | Potassium gluconate, anhydrous [10] | 80 | 1:4 |
| Example 1-P1 | Silver acetate, anhydrous [11] | 80 | Podium gluconate, anhydrous [4] | 20 | 4:1 |
| Example 1-P2 | Silver acetate, anhydrous [11] | 20 | Podium gluconate, anhydrous [4] | 80 | 1:4 |
| Example 1-P3 | Silver acetate, anhydrous [11] | 80 | d-Glucitol, anhydrous [2] | 20 | 4:1 |
| Example 1-P4 | Silver acetate, anhydrous [11] | 20 | d-Glucitol, anhydrous [2] | 80 | 1:4 |

[1, 7] = available from Niacet Corporation, Niagara Falls, NY, USA.
[2] = available from EMD Millipore, a division of Merck KGaA, Darmstadt, Germany.
[3, 4] = available from Jungbunzlauer Inc., Newton Centre, MA, USA.
[5] = available from Chem One Ltd., Houston, TX, USA.
[6] = available from Vasa Pharmachem Pvt. Ltd., Gujarat, India.
[8, 9, 11] = available from Sigma-Aldrich Corporation, St. Louis, MO, USA.
[10] = available from Jost Chemical Co., St. Louis, MO, USA.

The tablet binding compositions were flowable and easily mixed with other components of a cleaning/disinfectant formulation for tableting.

Example 2

Comparative Examples Using Traditional Tablet Binding Compounds

Tablets containing the traditional binding compounds boric acid or zeolites were prepared for comparison to tablets containing the tablet binding composition containing an acetate salt and C6 saccharide derivative sequestrant as provided herein. The formulations are provided in Tables 2 and 3.

TABLE 2

Example 2-A - Comparative Borate Detergent Formulation.

| Component | Weight (%) |
|---|---|
| Sodium carbonate [11] | 50 |
| Sodium percarbonate [12] | 9 |
| Citric acid [13] | 20 |
| Boric acid [14] | 15 |
| Alcohol ethoxylate [15] (BioSoft ® 25-7) | 1 |
| Sodium dodecylbenzene sulfonate [16] | 5 |
| Total = | 100 |

TABLE 3

Example 2-B - Comparative Zeolite Detergent Formulation.

| Component | Weight (%) |
|---|---|
| Sodium carbonate [11] | 50 |
| Sodium percarbonate [12] | 9 |
| Citric acid [13] | 20 |
| Sodium acetate [17] | 6.4 |
| Zeolite [18] (Valfor ® 100 Zeolite) | 6.4 |
| Alcohol ethoxylate [15] (BioSoft ® 25-7) | 3.2 |
| Sodium dodecylbenzene sulfonate [16] | 5 |
| Total = | 100 |

[11] = available from FMC Corporation, Philadelphia, PA, USA.
[12] = available from Solvay Chemicals, Bruxelles, Belgium.
[13] = available from Tate & Lyle PLC, London, UK.
[14] = available from American Borate Company, Virginia Beach, VA, USA.
[15, 16] = available from Stepan Company, Northfield, IL, USA.
[17] = available from Niacet Corporation, Niagara Falls, NY, USA.
[18] = available from PQ Corporation, Valley Forge, PA, USA.

Each example was made in a 225 gram batch. Powders and liquids individually were weighed out using a top load balance. A 500 mL beaker was used as a mixing vessel. The alcohol ethoxylate was mixed with either the boric acid (Example 2-A) or the zeolite (Example 2-B) to prepare a preblend. Mixing was performed manually using a metal spatula and the components were mixed for at least 1 minute and visually inspected to ensure homogenous mixing. The remaining ingredients of the formulation were added to the pre-blend and manually mixed using a metal spatula for at least 1 minute and visually inspected to ensure the powder blend was homogenous. If necessary, the mixing was continued until a homogeneous blend was obtained.

The homogeneous blend then was used to prepare tablets. 30 gram aliquots of the homogeneous blend of each formulation separately were weighed to be made into compressed tablets. The weight of each powder sample was recorded as "Original Weight" (see Table 4). Each 30 gram powder sample was compressed into a tablet using a 44.45 mm diameter die. Tablet compression was performed using a CARVER Press (Carver, Inc. (Wabash, Ind.)) with a 7500 PSI gauge. For each formulation, tablets were made at a low pressure of 1750 PSI, and at a high pressure of 5500 PSI.

After tablets compressed to their prescribed PSI were prepared, visual observations were made about tablet appearance and how well the tablets released from the die. These observations were recorded as "Tablet Appearance" (see Table 4). The tablets should eject smoothly from the die without sticking (e.g., there should be no tablet face sticking) and without leaving any material on the die (e.g., there should be no die wall streaking). The tablets should exhibit smooth face surfaces, good edges and good side walls with no or few visually detactable defects. In cases of failing formulations, tablets can become stuck in the die, or the tablets can fail to retain shape, or the tablets can delaminate or have defects on a face or side walls or both, or do not have good edges.

The compressed tablets were weighed and the results were recorded as "Tablet Weight" (see Table 4). Weight loss was determined by the difference between "Tablet Weight" and "Original Weight." Tablets that lose more than 0.5% of their original weight are indicative of tablets with poor tablet qualities like rough edges, die wall streaking and tablet face sticking.

Next, each tablet was crushed using a force gauge to determine the strength of the tablet. Hardness was measured using a Model DPS digital force gauge from Imada, Inc. (Northbrook, Ill., USA). Measurements were performed at room temperature (about 72° F.) at a relative humidity of about 26%. The force gauge was zeroed to tare the gauge. A tablet was placed in the gauge so that the tablet's face was perpendicular to the crushing platform and underneath the stem of the digital force gauge. Using a controlled, slow motion, the lever of the gauge was pulled down until either the tablet was broken or the digital force gauge reached 40 pounds. The peak measurement was recorded as "Tablet Hardness" (see Table 4).

Finally, a 1 gram sample of each example was dissolved in 100 mL of water using 140 mL glass beakers and observations were made regarding solution clarity. Solutions were subjectively evaluated via visual inspection and identified as either clear or cloudy. If a particulate formed, an indication of "precipitate" was recorded.

TABLE 4

Results for comparative formulations containing boric acid or zeolite.

| | Example 2-A: Boric Acid | Example 2-A: Boric Acid | Example 2-B: Zeolite | Example 2-B: Zeolite |
|---|---|---|---|---|
| | Compression: | | | |
| | 1750 PSI | 5500 PSI | 1750 PSI | 5500 PSI |
| Tablet Hardness (kPa) | 8.15 | 18.45 | 7.78 | 19.01 |
| Original Weight (g) | 30.07 | 30.01 | 30.18 | 30.12 |
| Tablet Weight (g) | 30.06 | 29.98 | 29.97 | 29.85 |
| Weight Lost (%) | 0.03 | 0.1 | 0.7 | 0.9 |
| Tablet Appearance | smooth face, good edges | smooth face, good edges | defects on face and side walls | defects on face and side walls |
| Solution Clarity | clear | clear | cloudy, precipitate | cloudy, precipitate |

The composition examples were flowable and capable of being compressed into tablets using the CARVER Press. The tablet industry has established a lower limit of 9 kPa and an upper limit of 23 kPa as the optimal operating range for tablet hardness. Both formulations were able to attain a tablet hardness value within this range when compressed at 5500 PSI. Neither formulation containing traditional tablet binding compounds (boric acid or zeolite), however, was able to achieve a tablet hardness within the optimal operating range when compressed at the very low compression pressure of 1750 PSI.

A weight loss percentage of more than 0.5% is indicative of poor aesthetic tablet quality because material is lost due to rough tablet edges, die wall streaking and sticking of the punch faces. The tablets produced from the formulation containing boric acid had good weight loss values and the tablets produced had smooth faces and good edges. The tablets produced from the formulation containing zeolite as a tablet binding compound exhibited defects on the face and side walls, and exhibited weight losses of greater than 0.5%. All of these results indicate poor tablet quality when zeolite was the tablet binding compound.

Finally, complete water solubility is a desired characteristic of tablet formulations for preparing cleaning and disinfecting solutions. The comparative formulation containing boric acid as the tablet binding compound was completely soluble in water and yielded a clear solution. The comparative formulation containing zeolite as the tablet binder yielded a cloudy solution with a noticeable precipitate. This is not unexpected, as it is well known that zeolites are not soluble in water. Therefore, boric acid as a tablet binding compound yields good quality tablets, but due to the overall concerns of borates, most companies are opting to remove borates completely from their formulations. While zeolites are often used as binders in tablets, they are not an acceptable replacement for borates, as the resulting tablets are of inferior quality and the solutions resulting from dissolution of the tablets are not clear, and the particulates due to the zeolites can leave a film or residue on a surface that has been cleaned with the solution in which zeolites are present.

Example 3

Detergent Formulations Containing 80:20 Acetate/Sequestrant Binding Composition Tablets containing the tablet binding compositions provided herein that include an acetate salt and a C6 saccharide derivative sequestrant were prepared. A ratio of 4:1 acetate to sequestrant was selected. Tablets were prepared that contained the same acetate salt (sodium acetate anhydrous) and different C6 saccharide derivative sequestrants (d-glucitol, mannitol, glucono-delta-lactone, and sodium gluconate). The formulations are provided in Table 5.

TABLE 5

Detergent Formulation containing 80:20 Acetate/Sequestrant

| Component | Example 3-A Weight (%) | Example 3-B Weight (%) | Example 3-C Weight (%) | Example 3-D Weight (%) |
|---|---|---|---|---|
| Sodium carbonate [11] | 50 | 50 | 50 | 50 |
| Sodium percarbonate [12] | 9 | 9 | 9 | 9 |
| Citric acid [13] | 20 | 20 | 20 | 20 |
| Acetate/C6 Saccharide Sequestrant Binding Composition: | | | | |
| From Example 1-A1 (Na acetate/d-glucitol, 4:1) | 15 | | | |
| From Example 1-N1 (Na acetate/mannitol, 4:1) | | 15 | | |

TABLE 5-continued

Detergent Formulation containing 80:20 Acetate/Sequestrant

| Component | Example 3-A Weight (%) | Example 3-B Weight ( % ) | Example 3-C Weight (%) | Example 3-D Weight (%) |
|---|---|---|---|---|
| From Example 1-B1 (Na acetate/glucono-delta-lactone, 4:1) | | | 15 | |
| From Example 1-C1 (Na acetate/Na gluconate, 4:1) | | | | 15 |
| Alcohol ethoxylate [15] (BioSoft ® 25-7) | 1 | 1 | 1 | 1 |
| Sodium dodecylbenzene sulfonate [16] | 5 | 5 | 5 | 5 |
| Total = | 100 | 100 | 100 | 100 |

[11] = available from FMC Corporation, Philadelphia, PA, USA.
[12] = available from Solvay Chemicals, Bruxelles, Belgium.
[13] = available from Tate & Lyle PLC, London, UK.
[15, 16] = available from Stepan Company, Northfield, IL, USA.

Each example was made in a 225 gram batch. Powders and liquids individually were weighed out using a top load balance. A 500 mL beaker was used as a mixing vessel. The alcohol ethoxylate was mixed with the binding composition to prepare a pre-blend. Mixing was performed manually using a metal spatula and the components were mixed for at least 1 minute and visually inspected to ensure homogenous mixing, resulting in a pre-blend. The remaining ingredients of the formulation were added to the pre-blend and manually mixed using a metal spatula for at least 1 minute and visually inspected to ensure the powder blend was homogenous. If necessary, the mixing was continued until a homogeneous blend was obtained.

The homogeneous blend then was used to prepare tablets. 30 gram aliquots of the homogeneous blend of each formulation separately were weighed to be made into compressed tablets. The weight of each powder sample was recorded (as "Original Weight," see Table 6). Each 30 gram powder sample was compressed into a tablet using a 44.45 mm diameter die. Tablet compression was performed using a CARVER Press (Carver, Inc. (Wabash, Ind.)) with a 7500 PSI gauge. For each formulation, tablets were made at a low pressure of 1750 PSI and at a high pressure of 5500 PSI.

After tablets compressed to their prescribed PSI were prepared, visual observations were made about tablet appearance and how well the tablets released from the die. These observations were recorded as "Tablet Appearance" (see Table 6). The compressed tablets were weighed and the results were recorded as "Tablet Weight" (see Table 6). Weight loss was determined by the difference between "Tablet Weight" and "Original Weight." Tablets that lose more than 0.5% of their original weight are indicative of tablets with poor tablet qualities.

Next, each tablet was crushed using a force gauge to determine the strength of the tablet. The hardness of the tablets was measured using a Model DPS digital force gauge from Imada, Inc. (Northbrook, Ill., USA) under the conditions and using the method described in Example 2. These results were recorded as "Tablet Hardness" (see Table 6).

Finally a 1 gram sample of each example was dissolved in 100 mL of water using 140 mL glass beakers and observations were made regarding solution clarity. Solutions were subjectively evaluated via visual inspection and identified as either clear or cloudy. An indication of 'precipitate' was recorded if a particulate formed.

TABLE 6

Results of Tablets Containing 4:1 Acetate:Sequestrant Binding Composition

| | Example 3-A: glucitol | | Example 3-B: mannitol | |
|---|---|---|---|---|
| | Compression: | | | |
| | 1750 PSI | 5500 PSI | 1750 PSI | 5500 PSI |
| Tablet Hardness (kPa) | 13.3 | 19.86 | 8.07 | 17.44 |
| Original Wt. (g) | 30 | 30.07 | 30.11 | 30.04 |
| Tablet Weight (g) | 29.98 | 30.03 | 30.06 | 30.03 |
| Weight Lost (%) | 0.07 | 0.13 | 0.17 | 0.03 |
| Tablet Appearance | smooth face, good edges | smooth face, good edges | smooth face, good edges | smooth face, good edges |
| Solution Clarity | clear | clear | clear | clear |

| | Example 3-C: glucono-delta-lactone | | Example 3-D: gluconate | |
|---|---|---|---|---|
| | Compression: | | | |
| | 1750 PSI | 5500 PSI | 1750 PSI | 5500 PSI |
| Tablet Hardness (kPa) | 12.34 | 17.62 | 10.74 | 18.14 |
| Original Wt. (g) | 30 | 30.15 | 29.99 | 30.03 |
| Tablet Weight (g) | 30 | 30.14 | 29.95 | 29.97 |
| Weight Lost (%) | 0 | 0.03 | 0.13 | 0.2 |
| Tablet Appearance | smooth face, good edges | smooth face, good edges | smooth face, good edges | smooth face, good edges |
| Solution Clarity | clear | clear | clear | clear |

All tablets containing the tablet binding compositions provided herein in which the ratio of acetate:sequestrant was 4:1, regardless of the C6 saccharide derivative sequestrant selected (d-glucitol, mannitol, glucono-delta-lactone or sodium gluconate) exhibited a hardness within the optimal operating range identified by the tablet industry, and had smooth faces and good edges when compressed at 5500 PSI. Formulations containing the tablet binding compositions provided herein containing d-glucitol, glucono-delta-lactone or sodium gluconate compressed at the low compression force of 1750 PSI produced tablets having a hardness within the optimal operating range, unlike formulations containing boric acid or zeolite as a tablet binding compound, which, when compressed at 1750 PSI, exhibited a tablet hardness below the optimal operating range. When dissolved, the tablets containing the tablet binding compositions provided herein produced clear solutions, similar to solutions in which boric acid was used as a binder. When compared to tablets containing zeolite as a binder, the clarity of the solutions produced using the tablet binding compositions provided herein yielded superior solutions, particularly with reference to solution clarity. The tablet binding compositions provided herein in which the ratio of acetate:sequestrant was 4:1 were suitable replacements for boric acid as a tablet binding compound.

Example 4

Detergent Formulations Containing 20:80 Acetate/Sequestrant Binding Composition

Tablets containing the tablet binding compositions provided herein that include an acetate salt and a C6 saccharide derivative sequestrant were prepared having a ratio of 1:4 acetate to sequestrant. Tablets were prepared containing the same acetate salt (sodium acetate anhydrous) and different C6 saccharide derivative sequestrants (d-glucitol, glucono-delta-lactone, and sodium gluconate). The formulations are provided in Table 7. The tablets were prepared and tested as set forth above in Example 3.

TABLE 7

Detergent Formulation containing 20:80 Acetate/Sequestrant

| Component | Example 4-A Weight (%) | Example 4-B Weight ( % ) | Example 4-C Weight (%) | Example 4-D Weight (%) |
|---|---|---|---|---|
| Sodium carbonate [11] | 50 | 50 | 50 | 50 |
| Sodium percarbonate [12] | 9 | 9 | 9 | 9 |
| Citric acid [13] | 20 | 20 | 20 | 20 |
| Acetate/C6 Saccharide Sequestrant Binding Composition: | | | | |
| From Example 1-A2 (Na acetate/d-glucitol, 1:4) | 15 | | | |
| From Example 1-N2 (Na acetate/mannitol, 1:4) | | 15 | | |
| From Example 1-B2 (Na acetate/glucono-delta-lactone, 1:4) | | | 15 | |
| From Example 1-C2 (Na acetate/Na gluconate, 1:4) | | | | 15 |
| Alcohol ethoxylate [15] (BioSoft ® 25-7) | 1 | 1 | 1 | 1 |
| Sodium dodecylbenzene sulfonate [16] | 5 | 5 | 5 | 5 |
| Total = | 100 | 100 | 100 | 100 |

[11] = available from FMC Corporation, Philadelphia, PA, USA.
[12] = available from Solvay Chemicals, Bruxelles, Belgium.
[13] = available from Tate & Lyle PLC, London, UK.
[15] = Versene ™ 220, available from Stepan Company, Northfield, IL, USA.
[16] = available from Stepan Company, Northfield, IL, USA.

The results for tablet hardness, weight loss and tablet appearance, and the clarity of the resulting solutions are presented in Table 8.

TABLE 8

Results of Tablets Containing 1:4 Acetate:Sequestrant Binding Composition

| | Example 4-A: glucitol | | Example 4-B: mannitol | |
|---|---|---|---|---|
| Compression: | 1750 PSI | 5500 PSI | 1750 PSI | 5500 PSI |
| Tablet Hardness (kPa) | 11.01 | 22.42 | 8.71 | 19.03 |
| Original Wt. (g) | 30.12 | 29.98 | 29.99 | 30.01 |
| Tablet Weight (g) | 30.11 | 29.98 | 29.97 | 29.96 |
| Weight Lost (%) | 0.03 | 0 | 0.1 | 0.17 |
| Tablet Appearance | smooth face, good edges | smooth face, good edges | smooth face, good edges | smooth face, good edges |
| Solution Clarity | clear | clear | clear | clear |

| | Example 4-C: glucono-delta-lactone | | Example 4-D: gluconate | |
|---|---|---|---|---|
| Compression: | 1750 PSI | 5500 PSI | 1750 PSI | 5500 PSI |
| Tablet Hardness (kPa) | 12.06 | 17.62 | 11.54 | 18.3 |
| Original Wt. (g) | 30.05 | 30.15 | 30.1 | 30.13 |
| Tablet Weight (g) | 30.01 | 30.14 | 30.02 | 30.09 |
| Weight Lost (%) | 0.13 | 0.03 | 0.27 | 0.13 |

TABLE 8-continued

Results of Tablets Containing 1:4 Acetate:Sequestrant Binding Composition

| | | | | |
|---|---|---|---|---|
| Tablet Appearance | smooth face, good edges | smooth face, good edges | smooth face, good edges | smooth face, good edges |
| Solution Clarity | clear | clear | clear | clear |

The tablets produced using the tablet binding compositions provided herein in which the ratio of acetate:sequestrant was 1:4 exhibited properties similar to those obtained produced using the tablet binding compositions provided herein in which the ratio of acetate:sequestrant was 4:1. All tablets containing the tablet binding compositions provided herein in which the ratio of acetate:sequestrant was 1:4, regardless of the C6 saccharide derivative sequestrant selected (d-glucitol, mannitol, glucono-delta-lactone or sodium gluconate) exhibited a hardness within the optimal operating range identified by the tablet industry and had smooth faces and good edges when compressed at 5500 PSI.

Formulations containing the tablet binding compositions provided herein containing d-glucitol, glucono-delta-lactone or sodium gluconate compressed at the low compression force of 1750 PSI produced tablets having a hardness within the optimal operating range, unlike formulations containing boric acid or zeolite as a binder, which, when compressed at 1750 PSI, exhibited a tablet hardness below the optimal operating range. Formulations containing mannitol as the C6 saccharide derivative sequestrant and compressed as 1750 PSI yielded tablets similar to or slightly harder than tablets in which boric acid was the binding compound. When dissolved, the tablets containing the tablet binding compositions provided herein produced clear solutions, similar to solutions in which boric acid was used as a tablet binding compound. When compared to tablets containing zeolite as a binder, the clarity of the solutions produced using the tablet binding compositions provided herein yielded superior solutions, particularly with reference to solution clarity. The tablet binding compositions provided herein in which the ratio of acetate: sequestrant was 1:4 were suitable replacements for boric acid as a tablet binding compound.

Example 5

Comparative Example Using C6 Saccharide Derivative Sequestrant Alone

Tablets containing only a C6 saccharide derivative sequestrant as a tablet binding compound were prepared to demonstrate that that results achieved for the acetate:C6 saccharide derivative sequestrant binding compositions provided herein could not be achieved using the C6 saccharide derivative sequestrant alone. The C6 saccharide derivative sequestrant selected was d-glucitol. The formulation is shown in Table 9.

TABLE 9

Detergent Formulation containing Glucitol alone as Binding Compound.

| Component | Example 5 Weight (%) |
|---|---|
| Sodium carbonate[11] | 50 |
| Sodium percarbonate[12] | 9 |
| Citric acid[13] | 20 |

TABLE 9-continued

| Detergent Formulation containing Glucitol alone as Binding Compound. | |
|---|---|
| Component | Example 5 Weight (%) |
| d-Glucitol[2] | 15 |
| Alcohol ethoxylate[15] (BioSoft ® 25-7) | 1 |
| Sodium dodecylbenzene sulfonate[16] | 5 |
| Total = | 100 |

[2]= available from EMD Millipore, a division of Merck KGaA, Darmstadt, Germany.
[11]= available from FMC Corporation, Philadelphia, PA, USA.
[12]= available from Solvay Chemicals, Bruxelles, Belgium.
[13]= available from Tate & Lyle PLC, London, UK.
[15, 16]= available from Stepan Company, Northfield, IL, USA.

The tablets were prepared and tested as set forth above in Example 3. The results for tablet hardness, weight loss and tablet appearance, and the clarity of the resulting solutions are presented in Table 10.

TABLE 10

| Results of Tablets Containing only d-Glucitol as Binding Compound. | | |
|---|---|---|
| | Compression | |
| | 1750 PSI | 5500 PSI |
| Tablet Hardness (kPa) | 0 | 25.05 |
| Original Weight (g) | 30.01 | 30 |
| Tablet Weight (g) | 24.91 | 29.52 |
| Weight Lost (%) | 16.99 | 1.6 |
| Tablet Appearance | tablet faces stuck in punch; tore in half | tablet stuck in die; bad side walls |
| Solution Clarity | clear | clear |

At a compression force of 1750 PSI, the detergent formulation containing only d-glucitol as the binding compound could not be compressed into a tablet. The tablet faces were stuck in the punch and the "tablet" tore in half when attempts were made to remove the material from the die. Even at higher compression forces, the resulting tablet exhibited significant weight loss and was stuck in the die. When removed from the die, the tablet had bad side walls and surface defects. The tablet hardness of the tablet containing only d-glucitol was outside the ideal operating range identified by the tablet industry because it was too hard. Tablets having a hardness greater than 23 kPa tend to exhibit poor dissolution properties. Glucitol alone does not demonstrate the same properties achieved using the tablet binding compositions provided herein, nor is glucitol alone a suitable replacements for boric acid as a tablet binder.

Example 6

Comparative Example Using Acetate Salt Alone as a Binding Compound

Tablets containing only sodium acetate as a binding compound were prepared to demonstrate that that results achieved for the acetate:C6 saccharide derivative sequestrant binding compositions provided herein could not be achieved using the acetate salt alone. The exemplary acetate salt selected was sodium acetate. The formulation is provided in Table 11.

TABLE 11

| Detergent Formulation containing Sodium Acetate alone. | |
|---|---|
| Component | Weight (%) |
| Sodium acetate, anhydrous[1] | 15 |
| Sodium carbonate[11] | 50 |
| Sodium percarbonate[12] | 9 |
| Citric acid[13] | 20 |
| Alcohol ethoxylate[15] (BioSoft ® 25-7) | 1 |
| Sodium dodecylbenzene sulfonate[16] | 5 |
| Total = | 100 |

[1]= available from Niacet Corporation, Niagara Falls, NY, USA.
[11]= available from FMC Corporation, Philadelphia, PA, USA.
[12]= available from Solvay Chemicals, Bruxelles, Belgium.
[13]= available from Tate & Lyle PLC, London, UK.
[15, 16]= available from Stepan Company, Northfield, IL, USA.

The tablets were prepared and tested as set forth above in Example 3. The results for tablet hardness, weight loss and tablet appearance, and the clarity of the resulting solutions are presented in Table 12.

TABLE 12

| Results of Tablets Containing Sodium Acetate Alone. | | |
|---|---|---|
| | Compression | |
| | 1750 PSI | 5500 PSI |
| Tablet Hardness (kPa) | 7.3 | 19.07 |
| Original Weight (g) | 30.08 | 29.99 |
| Tablet Weight (g) | 27.03 | 29.34 |
| Weight Lost (%) | 10.14 | 2.17 |
| Tablet Appearance | tablet stuck in die; bad side walls | tablet stuck in die; bad side walls |
| Solution Clarity | clear | clear |

At a compression force of 1750 PSI, the detergent formulation containing only sodium acetate as the binding compound formed a tablet that was outside the ideal operating range identified by the tablet industry because it was too soft. The tablet was stuck in the die and when removed exhibited bad side walls and surface defects, and exhibited high weight loss values. Even at higher compression forces, the resulting tablet exhibited significant weight loss and was stuck in the die. When removed from the die, the tablet had bad side walls and surface defects. Sodium acetate alone does not demonstrate the same properties achieved using the tablet binding compositions provided herein, nor is sodium acetate alone a suitable replacements for boric acid as a binder.

Example 7

Comparative Example Using EDTA as the Sequestrant

Tablets containing EDTA (ethylenediamine tetraacetic acid) as a sequestrant instead of a C6 saccharide derivative sequestrant were prepared to demonstrate that that results achieved for the acetate:C6 saccharide derivative sequestrant tablet binding compositions provided herein could not be achieved using an alternate sequestrant, such as EDTA, instead of the C6 saccharide derivative sequestrant as described herein in combination with an acetate salt. The formulation is provided in Table 13.

TABLE 13

| Detergent Formulation containing EDTA as binder. | |
|---|---|
| Component | Weight (%) |
| Sodium carbonate[11] | 50 |
| Sodium percarbonate[12] | 9 |
| Citric acid[13] | 20 |
| Alcohol ethoxylate[15] (BioSoft ® 25-7) | 1 |
| Sodium dodecylbenzene sulfonate[16] | 5 |
| EDTA[19] | 15 |
| Total = | 100 |

[11]= available from FMC Corporation, Philadelphia, PA, USA.
[12]= available from Solvay Chemicals, Bruxelles, Belgium.
[13]= available from Tate & Lyle PLC, London, UK.
[15, 16]= available from Stepan Company, Northfield, IL, USA.
[19]= available from Dow Chemical Company, Midland, MI, USA.

The tablets were prepared and tested as set forth above in Example 3. The results for tablet hardness, weight loss and tablet appearance, and the clarity of the resulting solutions are presented in Table 14.

TABLE 14

| Results of Tablets Containing EDTA as Binder. | Compression | |
|---|---|---|
| | 1750 PSI | 5500 PSI |
| Tablet Hardness (kPa) | 7.46 | 14.43 |
| Original Weight (g) | 30.09 | 30.16 |
| Tablet Weight (g) | 28.89 | 29.93 |
| Weight Lost (%) | 0.66 | 0.76 |
| Tablet Appearance | tablet had defects on face and side walls | tablet had defects on face and side walls |
| Solution Clarity | clear | clear |

At a compression force of 1750 PSI, the detergent formulation containing EDTA as the binder formed a tablet that was outside the ideal operating range identified by the tablet industry because it was too soft. The tablet was stuck in the die and when removed exhibited bad side walls and surface defects and exhibited high weight loss values. Even at higher compression forces, the resulting tablet exhibited significant weight loss and was stuck in the die. When removed from the die, the tablet had bad side walls and surface defects. EDTA does not demonstrate the same properties achieved using the tablet binding compositions provided herein, nor is EDTA a suitable replacements for boric acid as a binder.

Example 8

Comparative Example Detergent Formulation Containing Binder Outside of the Range of Ratios of 5:1-1:5

Tablets containing a ratio of acetate:C6 saccharide derivative sequestrant outside of the range of from about 5:1 to about 1:5 were prepared to demonstrate that that results achieved for the acetate:C6 saccharide derivative sequestrant tablet binding compositions provided herein in which the ratio of acetate:sequestrant is from about 5:1 to about 1:5 could not be achieved using a ratio above or below this range. The formulations are provided in Table 15.

TABLE 15

| Detergent Formulation containing 9:1 and 1:9 Acetate/Glucitol. | | |
|---|---|---|
| Component | Example 8-A (ratio 9:1) Weight (%) | Example 8-B (ratio 1:9) Weight (%) |
| Sodium acetate, anhydrous[1] | 13.5 | 1.5 |
| d-glucitol[2] | 1.5 | 13.5 |
| Sodium carbonate[11] | 50 | 50 |
| Sodium percarbonate[12] | 9 | 9 |
| Citric acid[13] | 20 | 20 |
| Alcohol ethoxylate[15] (BioSoft ® 25-7) | 1 | 1 |
| Sodium dodecylbenzene sulfonate[16] | 5 | 5 |
| Total = | 100 | 100 |

[1]= available from Niacet Corporation, Niagara Falls, NY, USA.
[2]= available from EMD Millipore, a division of Merck KGaA, Darmstadt, Germany.
[11]= available from FMC Corporation, Philadelphia, PA, USA.
[12]= available from Solvay Chemicals, Bruxelles, Belgium.
[13]= available from Tate & Lyle PLC, London, UK.
[15, 16]= available from Stepan Company, Northfield, IL, USA.

The tablets were prepared and tested as set forth above in Example 3. The results for tablet hardness, weight loss and tablet appearance, and the clarity of the resulting solutions are presented in Table 16.

TABLE 16

| Results of Tablets Containing 9:1 and 1:9 Acetate:Sequestrant blends. | Example 8-1: 9:1 acetate:glucitol | | Example 8-2: 1:9 acetate:glucitol | |
|---|---|---|---|---|
| Compression: | 1750 PSI | 5500 PSI | 1750 PSI | 5500 PSI |
| Tablet Hardness (kPa) | 6.89 | 17.75 | 0 | 19.32 |
| Original Weight (g) | 30.12 | 30.02 | 30.01 | 30 |
| Tablet Weight (g) | 29.99 | 29.32 | 27.39 | 29.64 |
| Weight Lost (%) | 0.43 | 2.33 | 8.73 | 1.2 |
| Tablet Appearance | tablet stuck in die; bad side walls | tablet stuck in die; bad side walls | tablet could not retain shape | tablet stuck in die; bad side walls |
| Solution Clarity | clear | clear | clear | clear |

At a compression force of 1750 PSI, the detergent formulation containing a ratio of 9:1 acetate:glucitol as the binder formed a tablet that was outside the ideal operating range identified by the tablet industry because it was too soft, while the formulation containing a ratio of 1:9 acetate:glucitol as the binder was unable to be formed into a tablet. At higher compression forces, all of the resulting tablets exhibit high weight loss values, the tablets were stuck in the die, and when removed from the die, the tablets had bad side walls and surface defects. Thus, using a ratio above or below the 5:1 to 1:5 ratio of acetate:C6 saccharide derivative sequestrant does not result in a binder that yields tablets having the properties achieved by the tableting binding compositions provided herein where the ratio of acetate:C6 saccharide derivative sequestrant is in the range of about 5:1 to about 1:5.

Example 9

Tablet Formation at Lower Compression Forces

As discussed above, tablets can be formed using the acetate:C6 saccharide derivative sequestrant binding formulation as described herein, having a ratio of acetate:sequestrant in the range of from about 5:1 to about 1:5 acetate to sequestrant using relatively low compression forces. The tablet hardness values for the tablets prepared as described in Examples 2 through 8 at a compression force of 1750 PSI are reproduced in Table 17.

TABLE 17

Hardness Values for Tablets Prepared Using 1750 PSI Compression.

| | Tablet Hardness | |
|---|---|---|
| | <9 kPa | Industry Standard (9 kPa-23 kPa) |
| Example 2-A = boric acid control | 8.15 | |
| Example 2-B = zeolite control | 7.78 | |
| Example 3-1 = 4:1 acetate:glucitol | | 13.3 |
| Example 3-2 = 4:1 acetate:lactone | | 12.34 |
| Example 3-3 = 4:1 acetate:gluconate | | 10.74 |
| Example 4-1 = 1:4 acetate:glucitol | | 11.01 |
| Example 4-2 = 1:4 acetate:lactone | | 12.06 |
| Example 4-3 = 1:4 acetate:gluconate | | 11.54 |
| Example 5 = glucitol only control | 0 | |
| Example 6 = Na acetate only control | 7.3 | |
| Example 7 = EDTA control | | 14.43 |
| Example 8-1 = 9:1 acetate glucitol | 6.89 | |
| Example 8-2 = 1:9 acetate:glucitol | 0 | |

All of the tablets that contained the tablet binding compositions as described herein, which have a range of ratios of acetate:C6 saccharide derivative sequestrant of from about 5:1 to about 1:5, had smooth faces and good edges, exhibited weight loss values of less than 0.5%, and had tablet hardness values within the optimal operating range (between 9 kPa and 23 kPa) when the tablets were prepared using the very low compression pressure of 1750 PSI.

This translates very well into the production process by reducing the compression needed to produce tablets that contain this tablet binding composition as well as eliminating the need for over-compression. Lower compression forces required to produce acceptable tablets can have significant impacts on the tableting process. For example, lower compression forces can reduce the wear of the dies and punches, and reduce the stress on the mechanical components and the drive train of the press. The lower compression forces also can reduce the expenses associated with maintenance and service of the press.

Although tablets containing EDTA as a binder exhibit a tablet hardness value within the optimal operating range when compressed at the very low compression pressure of 1750 PSI, the EDTA tablets had defects on their face and side walls and exhibited weight loss well above the acceptable values. This indicates that EDTA does not function well as a binder and indicates that it is not a suitable replacement for any of the C6 saccharide derivative sequestrants of the tablet binding compositions provided herein. The EDTA tablets exhibited a large amount of material lost through rough edges and tablet defects, making the tablets aesthetically unacceptable to consumers.

Example 10

Dishwasher Detergent Tablets

Tablets of a dishwasher detergent formulation were prepared using the acetate:C6 saccharide derivative sequestrant binding formulation as described herein, where the acetate was anhydrous sodium acetate and the C6 saccharide derivative sequestrant was anhydrous sodium gluconate anhydrous. The ratio of acetate to C6 saccharide derivative sequestrant was 1:5. The formulation is provided in Table 18.

TABLE 18

Dishwasher Detergent Tablet Formulation.

| Component | Weight (%) |
|---|---|
| Acetate/C6 Saccharide Sequestrant Binding Composition From Example 1-C7 (Na acetate/Na gluconate, 1:5) | 12 |
| Sodium carbonate[11] | 15 |
| Citric acid[13] | 35 |
| Sodium bisulfate[20] | 35 |
| Polyethylene glycol[21] | 3 |
| Total = | 100 |

[11]= available from FMC Corporation, Philadelphia, PA, USA.
[13]= available from Tate & Lyle PLC, London, UK.
[20]= available from Jones-Hamilton Co., Walbridge, OH, USA.
[21]= available from Dow Chemical Company, Midland, MI, USA.

The components were mixed in a 30 cubic foot V-blender for 15 to 20 minutes. 15 gram aliquots of the resulting homogeneous blend were transferred to a rotary style tablet press equipped with 1.28" diameter dies and compressed using a compression force of 12,000 PSI. Each of the resulting tablets had a weight of about 15 grams. The tablets had smooth faces and good edges, exhibited weight loss values of less than 0.5%, and had tablet hardness values between 7-15 kPa.

Example 11

General Purpose Cleaner Tablets

Tablets of a general purpose cleaner formulation were prepared using the acetate:C6 saccharide derivative sequestrant binding formulation as described herein, where the acetate was anhydrous sodium acetate and the C6 saccharide derivative sequestrant was anhydrous glucono-delta-lactone. The ratio of acetate to C6 saccharide derivative sequestrant was 1:5. The formulation is provided in Table 19.

TABLE 19

General Purpose Cleaner Tablet Formulation.

| Component | Weight (%) |
|---|---|
| Acetate/C6 Saccharide Sequestrant Binding Composition From Example 1-B7 (Na acetate/glucono-delta-lactone, 1:5) | 12 |
| Sodium carbonate[11] | 20 |
| Citric acid[13] | 10 |
| Alcohol ethoxylate[15] (BioSoft ® 25-7) | 1 |
| Sodium dodecylbenzene sulfonate[16] | 5 |
| Polyethylene glycol[21] | 5 |
| Sodium percarbonate[22] | 47 |
| Total = | 100 |

[11]= available from FMC Corporation, Philadelphia, PA, USA.
[13]= available from Tate & Lyle PLC, London, UK.
[15, 16]= available from Stepan Company, Northfield, IL, USA.
[21]= available from Dow Chemical Company, Midland, MI, USA.
[22]= available from Solvay North America LLC, Houston, TX, USA.

The components were mixed in a 30 cubic foot V-blender for 15 to 20 minutes. 20 gram aliquots of the resulting homogeneous blend were transferred to a rotary style tablet press equipped with 1.58" diameter dies and compressed using a compression force of 5500 PSI. Each of the tablets had a weight of about 20 grams. The tablets had smooth faces and good edges, exhibited weight loss values of less than 0.5%, and had tablet hardness values between 7-15 kPa.

Example 12

Floor Cleaner Tablets

Tablets of a floor cleaner formulation were prepared using the acetate:C6 saccharide derivative sequestrant binding formulation as described herein, where the acetate was anhydrous sodium acetate and the C6 saccharide derivative sequestrant was anhydrous glucono-delta-lactone. The ratio of acetate to C6 saccharide derivative sequestrant was 1:5. The formulation is provided in Table 20.

TABLE 20

Floor Cleaner Tablet Formulation.

| Component | Weight (%) |
|---|---|
| Acetate/C6 Saccharide Sequestrant Binding Composition From Example 1-B6 (Na acetate/glucono-delta-lactone, 5:1) | 7.8 |
| Sodium carbonate[11] | 15 |
| Citric acid[13] | 25 |
| Alcohol ethoxylate[15] (BioSoft ® 25-7) | 3 |
| Sodium dodecylbenzene sulfonate[16] | 5 |
| Polyethylene glycol[21] | 4.2 |
| Sodium percarbonate[22] | 40 |
| Total = | 100 |

[11]= available from FMC Corporation, Philadelphia, PA, USA.
[13]= available from Tate & Lyle PLC, London, UK.
[15, 16]= available from Stepan Company, Northfield, IL, USA.
[21]= available from Dow Chemical Company, Midland, MI, USA.
[22]= available from Solvay North America LLC, Houston, TX, USA.

The components were mixed in a 30 cubic foot V-blender for 15 to 20 minutes. 25 gram aliquots of the resulting homogeneous blend were transferred to a rotary style tablet press equipped with 1.58" diameter dies and compressed using a compression force of 14,000 PSI. Each of the tablets had a weight of about 25 grams. The tablets had smooth faces and good edges, exhibited weight loss values of less than 0.5%, and had tablet hardness values between 7-15 kPa.

Example 13

Garbage Disposal Cleaner Tablets

Tablets of a garbage disposal cleaner formulation were prepared using the acetate:C6 saccharide derivative sequestrant binding formulation as described herein, where the acetate was anhydrous sodium acetate and the C6 saccharide derivative sequestrant was anhydrous sodium gluconate. The ratio of acetate to C6 saccharide derivative sequestrant was 1:2.5. The formulation is provided in Table 21.

TABLE 21

Garbage Disposal Cleaner Tablet Formulation.

| Component | Weight (%) |
|---|---|
| Acetate/C6 Saccharide Sequestrant Binding Composition From Example 1-C6 (Na acetate/Na gluconate, 1:2.5) | 7 |
| Citric acid[13] | 33 |
| Sodium percarbonate[22] | 2 |
| Fragrance[23] | 1 |
| Ethoxylate surfactant (Tomadol ® 1-9)[24] | 1 |
| Sodium lauryl sulfonate[25] | 7 |
| Sodium bicarbonate[26] | 48 |
| Magnesium sterate[27] | 1 |
| Total = | 100 |

[13]= available from Tate & Lyle PLC, London, UK.
[22]= available from Solvay North America LLC, Houston, TX, USA.
[23]= available from Fragrance Design, LLC, Marietta, GA, USA.
[24]= available from Air Products and Chemicals, Inc., Allentown, PA, USA.
[25]= available from Huntsman Corp., The Woodlands, TX, USA.
[26]= available from Natrium Products, Cortland, NY, USA.
[27]= available from Univar USA Inc., Strongsville, OH, USA.

The components were mixed in a 30 cubic foot V-blender for 15 to 20 minutes. 40 gram aliquots of the resulting homogeneous blend were transferred to a rotary style tablet press equipped with 1.5" diameter dies and compressed using a compression force of 12,000 PSI. Each of tablets had a weight of about 40 grams. The tablets had smooth faces and good edges, exhibited weight loss values of less than 0.5%, and had tablet hardness values between 7-15 kPa.

While various embodiments of the subject matter provided herein have been described, it should be understood that they have been presented by way of example only, and not limitation. Since modifications will be apparent to those of skill in this art, it is intended that this invention be limited only by the scope of the appended claims.

The invention claimed is:

1. A tablet binding composition, comprising:

an acetate salt having a particle size greater than 200 μm in an amount from 15% to about 85% by weight of the composition; and a C6 saccharide derivative sequestrant having a particle size greater than 200 μm in an amount from about 15% to about 85% by weight of the composition, wherein the C6 saccharide derivative sequestrant is an amino hexose, a hexitol, an aldonic acid, an aldonic acid lactone, a hexose-delta-lactone, or a saccharic acid or a salt of any of these compounds or a combination thereof, wherein:

the ratio of the acetate salt to the C6 saccharide derivative sequestrant is in the range of about 5:1 to about 1:5; and the composition binds together ingredients in a tablet after application of a compression force.

2. The tablet binding composition of claim 1, wherein the acetate salt is in an anhydrous form.

3. The tablet binding composition of claim 1, wherein the acetate salt is water soluble.

4. The tablet binding composition of claim 1, wherein the acetate salt is sodium acetate, potassium acetate, calcium acetate, magnesium acetate, or silver acetate or a combination thereof.

5. The tablet binding composition of claim 1, wherein the C6 saccharide derivative sequestrant is one or a combination of an amino hexose selected from the group consisting of glucosamine, galactosamine, mannosamine and fucosamine and salts thereof.

6. The tablet binding composition of claim 1, wherein the C6 saccharide derivative sequestrant is a hexitol selected from the group consisting of allitol, altritol (talitol), fucitol, galactitol (dulcitol), glucitol (sorbitol), iditol, and mannitol and combinations thereof.

7. The tablet binding composition of claim 1, wherein the C6 saccharide derivative sequestrant is one or a combination of aldonic acids selected from the group consisting of allonic acid, altronic acid, fuconic acid, galactonic acid, gluconic acid, gulonic acid, idonic acid, mannonic acid, sorbonic acid and talonic acid and salts thereof.

8. The tablet binding composition of claim 1, wherein the C6 saccharide derivative sequestrant is one or a combination of aldonic acid lactones selected from the group consisting of allonolactone, altronolactone, gluconolactone, mannolactone, gulonolactone, idonolactone, galactonolactone, talonolactone and salts thereof.

9. The tablet binding composition of claim 1, wherein the C6 saccharide derivative sequestrant is one or a combination of hexose-delta-lactones selected from the group consisting of glucono-delta-lactone, galactono-delta-lactone and mannono-delta-lactone.

10. The tablet binding composition of claim 1, wherein the C6 saccharide derivative sequestrant is a saccharic acid selected from the group consisting of glucaric acid, galactaric acid and mannaric acid and salts thereof and any combination thereof.

11. The tablet binding composition of claim 1, wherein the C6 saccharide derivative sequestrant is sodium gluconate, glucono-delta-lactone or d-glucitol or a salt thereof or any combination thereof.

12. The tablet binding composition of claim 1, wherein:

the acetate salt is selected from the group consisting of sodium acetate, potassium acetate, calcium acetate, magnesium acetate and silver acetate and combinations thereof; and the C6 saccharide derivative sequestrant is fucosamine, glucosamine, galactosamine, mannosamine, allitol, altritol, fucitol, galactitol, glucitol, iditol, mannitol, allonic acid, altronic acid, fuconic acid, galactonic acid, gluconic acid, gulonic acid, idonic acid, mannonic acid, sorbonic acid, talonic acid, potassium allonate, potassium altronate, potassium fuconate, potassium galactonate, potassium gluconate, potassium gulonate, potassium idonate, potassium mannonate, potassium sorbonate, potassium talonate, sodium allonate, sodium altronate, sodium fuconate, sodium galactonate, sodium gluconate, sodium gulonate, sodium idonate, sodium mannonate, sodium sorbonate, sodium talonate, allonolactone, altronolactone, gluconolactone, mannolactone, gulonolactone, idonolactone, galactonolactone, talonolactone, glucono-delta-lactone, glucaric acid, galactaric acid, mannaric acid, potassium glucarate, or sodium glucarate or any combination thereof.

13. The tablet binding composition of claim 1, wherein the acetate salt is sodium acetate, potassium acetate, magnesium acetate, or silver acetate or a combination thereof.

14. A tablet, comprising a tablet binding composition that comprises:

an acetate salt having a particle size greater than 200 μm wherein the acetate salt is present in an amount from 15% to about 85% by weight of the tablet binding composition; and a C6 saccharide derivative sequestrant that is an amino hexose, a hexitol, an aldonic acid, an aldonic acid lactone, a hexose-delta-lactone, or a saccharic acid or a salt of any of these compounds or a combination thereof, having a particle size greater than 200 μm, wherein:

the ratio of the acetate salt to the C6 saccharide derivative sequestrant is in the range of about 5:1 to about 1:5; and the tablet binding composition is present in an amount of from about 0.5% to about 25% by weight of the tablet.

15. The tablet of claim 14, further comprising a fragrance in an amount of up to about 25% by weight of the tablet.

16. The tablet of claim 14, further comprising a liquid component selected from the group consisting of water, alcohols, glycols, polyglycols, glycol ethers, propanediols, glycerin, esters, terpenes, anionic surfactants, amphoteric surfactants, cationic surfactants, nonionic surfactants, zwitterionic surfactants, and combinations thereof in an amount from about 0.1% to about 10% by weight of the tablet.

17. The tablet of claim 14, further comprising a surfactant selected from among the group consisting of a nonionic, semi-polar nonionic, anionic, cationic, amphoteric and zwitterionic surfactant and combinations thereof, wherein:

the surfactant is water-soluble or water-dispersible; and the surfactant is present in an amount from about 0.1% to about 50% by weight of the tablet.

18. The tablet of claim 14, further comprising an excipient selected from the group consisting of diluents, glidants, flow aids, lubricants, disintegrants, pigments and colorants and combinations thereof in an amount from about 0.1% to about 60% by weight of the tablet.

19. The tablet of claim 14, further comprising an ingredient that is an enzyme, a bleaching agent, sodium perborate, sodium percarbonate, an expanded sodium percarbonate, an expanded sodium perborate, a bleach activator, an acid, a foam booster, a carbonate, a bicarbonate, a phosphate, an anti-microbial agent, a wetting agent, a dispersing agent, a hydrotrope, a polymer, a rheology control agent, a chelating agent, a pH modifier, a foam suppressant, or an anti-corrosion agent or any combination thereof, wherein the ingredient is present in the range of about 0.05% to 75% by weight of the tablet.

20. The tablet of claim 19, wherein the acid is selected from the group consisting of acetic, adipic, azelaic, citric, fumaric, glutaric, maleic, malonic, oxalic, pimelic, suberic, sebacic, and succinic acid and combinations thereof.

21. The tablet of claim 19, wherein the enzyme is selected from the group consisting of amylases, cellulases, lipases, and proteases and combinations thereof.

22. The tablet of claim 19, wherein the phosphate is selected from the group consisting of sodium acid pyrophosphate, monosodium phosphate, disodium phosphate, and sodium dihydrogen orthophosphate and combinations thereof.

23. The tablet of claim 19, wherein the foam booster is selected from the group consisting of fatty acid amides, alkoxylated fatty acid amides, fatty acid amides of alkanolamines, fatty acid amides of alkoxylated alkanolamines, and fatty acid amides of alkanolamide esters and combinations thereof.

24. The tablet of claim 19, wherein the beaching agent is selected from the group consisting of calcium peroxide, magnesium peroxide, diperoxy-dodecanedioic acid, magnesium monoperoxyphthalate hexahydrate, nonyl amino-6-oxoperoxysuccinic acid, a magnesium salt of meta-chloro-perbenzoic acid, urea peroxide, sodium percarbonate monohydrate, sodium carbonate peroxyhydrate, and sodium pyrophosphate peroxyhydrate and combinations thereof, wherein the bleaching agent is present in an amount of from about 0.05% to about 50% by weight of the tablet.

25. The tablet of claim 19, wherein the bleach activator is selected from the group consisting of decanoyloxybenzenecarboxylic acid (DOBA), nonanoyloxybenzene sulfonate (NOBS) and tetraacetylethylenediamine (TAED) and combinations thereof.

26. The tablet of claim 14, further comprising sodium percarbonate and tetra-acetylethylenediamine (TAED), wherein each of the sodium percarbonate and the TAED separately is present in an amount of from about 0.05% to about 50% by weight of the tablet.

27. The tablet of claim 19, further comprising a polymer coating applied to the surface of the tablet, wherein the polymer coating comprises adipic acid, azelaic acid, glutaric acid, malonic acid, oxalic acid, pimelic acid, sebacic acid, suberic acid, succinic acid, undecanedioic acid, dodecanedioic acid, tridecanedioic acid, hydroxypropyl cellulose, hydroxypropylmethyl cellulose, polyvinylacetate, hydroxyethyl cellulose, methylhydroxyethyl cellulose, methyl cellulose, ethyl cellulose, cellulose acetate, sodium carboxymethylcellulose, polymers and copolymers of acrylic acid and methacrylic acid and esters thereof, or polyvinylpyrrolidone or combinations thereof.

28. An article of manufacture, comprising:

a tablet containing the tablet binding composition of claim 1; and (a) a container suitable for containing the tablet; or (b) a set of instructions for preparing a cleaning/disinfectant solution by dissolving the tablet in a solvent; or (c) a set of instructions for storing the tablet; or (d) a material safety data sheet; or (e) a dispenser or applicator for a solution prepared by dissolution of the tablet; or (f) any combination of two or more of (a), (b), (c), (d) and (e).

* * * * *